(12) United States Patent
Hoshino et al.

(10) Patent No.: US 9,533,944 B2
(45) Date of Patent: *Jan. 3, 2017

(54) METHOD FOR PRODUCING OXIME

(71) Applicant: Sumitomo Chemical Company, Tokyo (JP)

(72) Inventors: Masahiro Hoshino, Oita (JP); Yuta Kikuchi, Osaki (JP); Sho Tsujiuchi, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/655,514

(22) PCT Filed: Dec. 12, 2013

(86) PCT No.: PCT/JP2013/084002
§ 371 (c)(1),
(2) Date: Jun. 25, 2015

(87) PCT Pub. No.: WO2014/103850
PCT Pub. Date: Jul. 3, 2014

(65) Prior Publication Data
US 2015/0353478 A1    Dec. 10, 2015

(30) Foreign Application Priority Data

Dec. 27, 2012  (JP) ................. 2012-284307
Feb. 15, 2013  (JP) ................. 2013-027440

(51) Int. Cl.
*C07C 249/04* (2006.01)
*C07D 201/04* (2006.01)

(52) U.S. Cl.
CPC .......... *C07C 249/04* (2013.01); *C07D 201/04* (2013.01); *C07C 2101/14* (2013.01)

(58) Field of Classification Search
CPC ................................................... C07C 249/04
See application file for complete search history.

(56) References Cited

U.S. PATENT DOCUMENTS

| 6,703,501 | B1 * | 3/2004 | Kim | ............ | C07D 201/04 540/536 |
| 7,232,784 | B2 * | 6/2007 | Kim | ............ | B01J 29/049 502/100 |
| 2004/0116746 | A1 | 6/2004 | Ono et al. | | |

FOREIGN PATENT DOCUMENTS

| CN | 1835800 A | 9/2006 |
| CN | 102000555 A | 4/2011 |
| CN | 102627286 A | 8/2012 |
| EP | 0395046 A2 | 10/1990 |
| EP | 1655070 A1 | 5/2006 |
| JP | H02295956 A | 12/1990 |
| JP | 2003064038 A | 3/2003 |
| JP | 2013189414 A | 9/2013 |
| WO | 2005009613 A1 | 2/2005 |
| WO | 2013125324 A1 | 8/2013 |

OTHER PUBLICATIONS

International Search Report issued Jan. 21, 2014 in International Application No. PCT/JP2013/084002.
International Preliminary Report on Patentability issued Jun. 30, 2015 in International Application No. PCT/JP2013/084002.
Rakottyay et al., "Oxidation of Amines Over Alumina Based Catalysts", Applied Catalysis A: General, vol. 378, No. 1, pp. 33-41 (Apr. 15, 2010).
Extended European Search Report issued Jul. 4, 2016 in EP Application No. 13866840.5.
Office Action issued Apr. 28, 2016 in CN Application No. 201380067841.8.
Rakottyay et al., "Oxidation of cyclohexylamine over modified alumina by molecular oxygen," Applied Catalysis A: General, vol. 367, pp. 32-38 (2009).
Xiaoyin et al., "Direct synthesis of clyclohexanone oxime from cyclohexanone (II) the effect of surface activity of Ti-PILC on ammoximation," Specialty Chemicals, Issue 1, pp. 44-46 (1996).

* cited by examiner

*Primary Examiner* — Golam M M Shameem
(74) *Attorney, Agent, or Firm* — Panitch Schwarze Belisario & Nadel LLP

(57) ABSTRACT

Provided is a method for producing an oxime compound with satisfactory selectivity. Provide is a method for producing an oxime represented by the following formula (II):

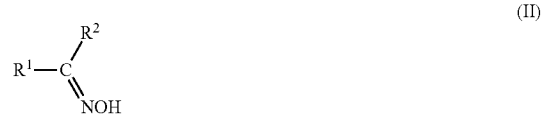

wherein $R^1$ and $R^2$ are respectively the same as defined below, the method including oxidizing an amine represented by the following formula (I):

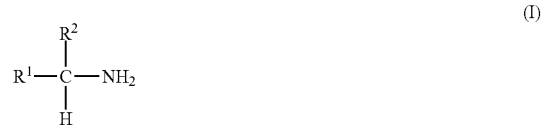

wherein $R^1$ and $R^2$ each independently represents a hydrogen atom, an optionally substituted hydrocarbon group, or an optionally substituted heterocyclic group (provided that $R^1$ and $R^2$ are not simultaneously hydrogen atoms), or $R^1$ and $R^2$, together with the carbon atom to which $R^1$ and $R^2$ are attached, form an optionally substituted alicyclic hydrocarbon group having 3 to 12 carbon atoms [hereinafter sometimes referred to as the amine compound (I)], with oxygen in the presence of a layered silicate.

7 Claims, No Drawings

METHOD FOR PRODUCING OXIME

CROSS-REFERENCE TO RELATED APPLICATION

This application is a Section 371 of International Application No. PCT/JP2013/084002, filed Dec. 12, 2013, which was published in the Japanese language on Jul. 3, 2014, under International Publication No. WO 2014/103850 A1, and the disclosure of which is incorporated herein by reference.

TECHNICAL FIELD

The present invention relates to a method for producing an oxime represented by the below-mentioned formula (II) [hereinafter sometimes referred to as the oxime compound (II)].

BACKGROUND ART

An oxime is useful as a starting material of a lactam, and also a starting material of a synthetic fiber. WO 2005/009613 A describes, as a method for producing the oxime compound (II), for example, a method in which a primary amine is oxidized with oxygen in the copresence of a hydrazyl radical or a hydrazine compound, and an oxidation promoter such as titanium oxide.

DISCLOSURE OF THE INVENTION

Problems to be Solved by the Invention

However, the above-mentioned method was not necessarily satisfactory in view of selectivity of the oxime compound (II). An object of the present invention is to provide a method for producing the oxime compound (II) with satisfactory selectivity.

Means for Solving the Problems

The present inventors have intensively studied so as to achieve the above object, and thus the present invention has been completed.

The present invention includes the following configurations.

(1) A method for producing an oxime represented by the following formula (II):

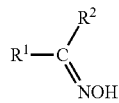
(II)

wherein $R^1$ and $R^2$ are respectively the same as defined below, the method comprising oxidizing an amine [hereinafter sometimes referred to as the amine compound (I)] represented by the following formula (I):

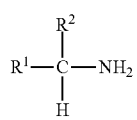
(I)

wherein $R^1$ and $R^2$ each independently represents a hydrogen atom, an optionally substituted hydrocarbon group, or an optionally substituted heterocyclic group (provided that $R^1$ and $R^2$ are not simultaneously hydrogen atoms), or $R^1$ and $R^2$, together with the carbon atom to which $R^1$ and $R^2$ are attached, form an optionally substituted alicyclic hydrocarbon group having 3 to 12 carbon atoms, with oxygen in the presence of a layered silicate.

(2) The method according to the above (1), wherein the layered silicate is smectite.

(3) The method according to the above (1) or (2), wherein the layered silicate contains at least one selected from the group consisting of hydrogen ions, ammonium ions, quaternary ammonium ions, cations of group 4 metal elements, cations of group 5 metal elements, cations of group 6 metal elements, germanium ions, oxides of positively charged group 4 metal elements, oxides of positively charged group 5 metal elements, oxides of positively charged group 6 metal elements, and positively charged germanium oxides.

(4) The method according to the above (1) or (2), wherein the layered silicate contains at least one selected from the group consisting of cations of group 4 metal elements, germanium ions, oxides of positively charged group 4 metal elements, and positively charged germanium oxides.

(5) The method according to the above (1) or (2), wherein the layered silicate contains at least one selected from the group consisting of titanium ions, germanium ions, positively charged titanium oxides, and positively charged germanium oxides.

(6) The method according to any one of the above (3) to (5), wherein the layered silicate further contains at least one selected from the group consisting of cations of group 8 metal elements, cations of group 9 metal elements, cations of group 10 metal elements, cations of group 11 metal elements, cations of group 12 metal elements, cations of group 13 metal elements, oxides of positively charged group 8 metal elements, oxides of positively charged group 9 metal elements, oxides of positively charged group 10 metal elements, oxides of positively charged group 11 metal elements, oxides of positively charged group 12 metal elements, oxides of positively charged group 13 metal elements, and oxides of positively charged silicon.

(7) The method according to any one of the above (1) to (6), wherein the layered silicate is calcined at 150 to 600° C.

(8) A method for producing an amide represented by the following formula (III):

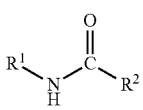
(III)

wherein $R^1$ and $R^2$ each independently represents a hydrogen atom, an optionally substituted hydrocarbon group, or an optionally substituted heterocyclic group (provided that $R^1$ and $R^2$ are not simultaneously hydrogen atoms), or $R^1$ and $R^2$, together with the nitrogen atom to which $R^1$ is attached and the carbon atom to which $R^2$ is attached, form an optionally substituted alicyclic hydrocarbon group having 3 to 12 carbon atoms [hereinafter sometimes referred to as the amine compound (III)], the method comprising subjecting the oxime represented by the above formula (II) produced by the method according to any one of the above (1) to (7) to the Beckmann rearrangement reaction.

Effects of the Invention

According to the present invention, the oxime compound (II) can be produced with satisfactory selectivity by oxidizing the amine compound (I) with oxygen.

MODE FOR CARRYING OUT THE INVENTION

The present invention will be described in detail below. In the present invention, the oxime compound (II) is produced by oxidizing the amine compound (I) with oxygen in the presence of a layered silicate.

In the formula (I), (II), and (III), when $R^1$ and $R^2$ each independently represents a hydrogen atom, an optionally substituted hydrocarbon group, or an optionally substituted heterocyclic group, $R^1$ and $R^2$ are not simultaneously hydrogen atoms. Here, "optionally substituted" refers to a hydrocarbon group or a heterocyclic group in which hydrogen atoms in a hydrocarbon group or a heterocyclic group may be partially or entirely substituted with a substituent. In $R^1$ and $R^2$, examples of the hydrocarbon group include an alkyl group, an alkenyl group, an alkynyl group, a cycloalkyl group, a cycloalkenyl group, an aryl group, and the like.

The alkyl group is preferably an alkyl group having 1 to 24 carbon atoms, and examples thereof include a methyl group, an ethyl group, a propyl group, an isopropyl group, a butyl group, an isobutyl group, an s-butyl group, a t-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, an eicosyl group, a henicosyl group, a heneicosyl group, a docosyl group, a tricosyl group, a tetracosyl group, and the like.

The alkenyl group is preferably an alkenyl group having 2 to 24 carbon atoms, and examples thereof include a vinyl group, an allyl group, a 2-methylallyl group, an isopropenyl group, a 1-propenyl group, a 1-butenyl group, a 2-butenyl group, a 3-butenyl group, a 1-methyl-1-propenyl group, a 1-methyl-2-propenyl group, a 2-methyl-1-propenyl group, a 2-methyl-2-propenyl group, a 1-pentenyl group, a 2-pentenyl group, a 3-pentenyl group, a 4-pentenyl group, a 1-methyl-1-butenyl group, a 2-methyl-1-butenyl group, a 3-methyl-1-butenyl group, a 1-methyl-2-butenyl group, a 2-methyl-2-butenyl group, a 3-methyl-2-butenyl group, a 1-hexenyl group, a 2-hexenyl group, a 3-hexenyl group, a 4-hexenyl group, a 5-hexenyl group, a 1-methyl-1-pentenyl group, a 2-methyl-1-pentenyl group, a 4-methyl-3-pentenyl group, a 2-ethyl-1-butenyl group, a 2-heptenyl group, a 2-octenyl group, a 2-nonenyl group, a 2-decenyl group, a 2-undecenyl group, a 2-dodecenyl group, a 2-tridecenyl group, a 2-tetradecenyl group, a 2-pentadecenyl group, a 2-hexadecenyl group, a 2-heptadecenyl group, a 2-octadecenyl group, a 2-nonadecenyl group, a 2-icosenyl group, a 2-eicosenyl group, a 2-henicosenyl group, a 2-heneicosenyl group, a 2-dococenyl group, a 2-tricosenyl group, a 2-tetracosenyl group, and the like.

The alkynyl group is preferably an alkynyl group having 2 to 24 carbon atoms, and examples thereof include an ethynyl group, a 1-propynyl group, a 2-propynyl group, a 1-butynyl group, a 2-butynyl group, a 3-butynyl group, a 1-methyl-2-propynyl group, a 1-pentynyl group, a 2-pentynyl group, a 3-pentynyl group, a 4-pentynyl group, a 1-methyl-3-butynyl group, a 2-methyl-3-butynyl group, a 1-hexynyl group, a 2-hexynyl group, a 3-hexynyl group, a 4-hexynyl group, a 5-hexynyl group, a 2-heptynyl group, a 2-octynyl group, a 2-nonynyl group, a 2-decynyl group, a 2-undecynyl group, a 2-dodecynyl group, a 2-tridecynyl group, a 2-tetradecynyl group, a 2-pentadecynyl group, a 2-hexadecynyl group, a 2-heptadecynyl group, a 2-octadecynyl group, a 2-nonadecynyl group, a 2-icosynyl group, a 2-eicosynyl group, a 2-henicosynyl group, a 2-heneicosynyl group, a 2-docosynyl group, a 2-tricosynyl group, a 2-tetracosynyl group, and the like.

The cycloalkyl group is preferably a cycloalkyl group having 3 to 8 carbon atoms, and examples thereof include a cyclopropyl group, a cyclobutyl group, a cyclopentyl group, a cyclohexyl group, a cycloheptyl group, a cyclooctyl group, and the like.

The cycloalkenyl group is preferably a cycloalkenyl group having 3 to 8 carbon atoms, and examples thereof include a cyclopropenyl group, a cyclobutenyl group, a cyclopentenyl group, a cyclohexenyl group, a cycloheptenyl group, a cyclooctenyl group, and the like.

Examples of the aryl group include a phenyl group, naphthyl group, an anthracenyl group, a phenanthryl group, a tolyl group, a xylyl group, and the like.

When the hydrocarbon group is an alkyl group, an alkenyl group, or an alkynyl group, examples of the substituent thereof include halogen atoms such as fluorine, chlorine, and bromine atoms; cycloalkyl groups having 3 to 6 carbon atoms, such as a cyclopropyl group, a 1-methylcyclopropyl group, a cyclobutyl group, a cyclopentyl group, a 1-methylcyclopentyl group, and a cyclohexyl group; alkoxy groups having 1 to 4 carbon atoms, such as a methoxy group, an ethoxy group, a propoxy group, an isopropoxy group, a butoxy group, an s-butoxy group, an isobutoxy group, and a t-butoxy group; thioalkoxy group having 1 to 4 carbon atoms, such as a thiomethoxy group, a thioethoxy group, a thiopropoxy group, and a thiobutoxy group; alkenyloxy groups having 3 to 4 carbon atoms, such as an allyloxy group, a 2-propenyloxy group, a 2-butenyloxy group, and a 2-methyl-3-propenyloxy group; aralkyloxy groups having 7 to 20 carbon atoms; aryl groups having 6 to 18 carbon atoms, such as a phenyl group, a naphthyl group, an anthracenyl group, and a phenanthryl group; aryloxy groups such as a phenyloxy group and a naphthyloxy group; alkanoyl groups having 2 to 7 carbon atoms; aryloyl groups having 7 to 19 carbon atoms; alkoxycarbonyl groups having 1 to 6 carbon atoms; and the like. When the hydrocarbon group is an alkyl group, examples of the alkyl group substituted with an aryl group having 6 to 18 carbon atoms include aralkyl groups such as a benzyl group, a phenethyl group, a 3-phenylpropyl group, a benzhydryl group, a trityl group, a triphenylethyl group, a (1-naphthyl)methyl group, and a (2-naphthyl) methyl group.

In $R^1$ and $R^2$, when the hydrocarbon group is a cycloalkyl group, a cycloalkenyl group, or an aryl group, examples of the substituent include the above-mentioned halogen atoms; cycloalkyl groups having 3 to 6 carbon atoms; alkoxy groups having 1 to 4 carbon atoms; thioalkoxy groups having 1 to 4 carbon atoms; alkenyloxy groups having 3 to 4 carbon atoms; aralkyloxy groups having 7 to 20 carbon atoms; aryl groups having 6 to 18 carbon atoms; aryloxy groups; alkanoyl groups having 2 to 7 carbon atoms; aryloyl groups having 7 to 19 carbon atoms; alkoxycarbonyl groups having 1 to 6 carbon atoms; alkyl groups having 1 to 6 carbon atoms, such as a methyl group, an ethyl group, a propyl group, an isopropyl group, a butyl group, an isobutyl group, an s-butyl group, a t-butyl group, a pentyl group, and a hexyl group; alkenyl groups having 2 to 6 carbon atoms, such as a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, 1-hexenyl group, a 2-hexenyl group, a 3-hexenyl group, a 4-hexenyl group, and a 5-hexenyl group; aralkyl groups having 7 to 20 carbon atoms, such as a benzyl group, a phenethyl group, and a naphthylmethyl group; and the like.

In $R^1$ and $R^2$, examples of the heterocyclic group include a heteroaryl group, a heteroaralkyl group, and the like. The heteroaryl group is preferably a heteroaryl group having 3 to 9 carbon atoms, and examples thereof include a pyridyl group, a quinonyl group, a pyrrolyl group, an imidazolyl group, a furyl group, an indolyl group, a thienyl group, an oxazolyl group, and the like. The heteroaralkyl group is preferably a heteroaralkyl group having 5 to 10 carbon atoms, and examples thereof include a pyridylmethyl group, a quinolylmethyl group, an indolylmethyl group, a furylmethyl group, a pyrrolylmethyl group, and the like.

When $R^1$ and $R^2$ are heterocyclic groups, examples of the substituent include the above-mentioned halogen atoms; cycloalkyl groups having 3 to 6 carbon atoms; alkoxy groups having 1 to 4 carbon atoms; thioalkoxy groups having 1 to 4 carbon atoms; alkenyloxy groups having 3 to 4 carbon atoms; aralkyloxy groups having 7 to 20 carbon atoms; aryl groups having 6 to 18 carbon atoms; aryloxy groups; alkanoyl groups having 2 to 7 carbon atoms; aryloyl groups having 7 to 19 carbon atoms; alkoxycarbonyl groups having 1 to 6 carbon atoms; alkyl groups having 1 to 6 carbon atoms; alkenyl groups having 2 to 6 carbon atoms; aralkyl groups having 7 to 20 carbon atoms; and the like.

In the formula (I), when $R^1$ and $R^2$ each independently represents a hydrogen atom or an optionally substituted hydrocarbon group, examples of the amine compound (I) include methylamine, ethylamine, n-propylamine, isopropylamine, n-butylamine, isobutylamine, s-butylamine, t-butylamine, pentylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, nonadecylamine, icosylamine, eicosylamine, henicosylamine, heneicosylamine, docosylamine, tricosylamine, tetracosylamine, 1-methylbutylamine, 2-methylbutylamine, cyclopropylmethylamine, cyclohexylmethylamine, benzylamine, 2-methylbenzylamine, 4-methylbenzylamine, 1-phenylethylamine, 2-phenylethylamine, 3-aminomethylpyridine, 1-(4-chlorophenyl)ethylamine, 2-(2-chlorophenyl)ethylamine, 1-(3-methoxyphenyl)ethylamine, 1-(4-methoxyphenyl)ethylamine, 2-(2-methoxyphenyl)ethylamine, 2-(3-methoxyphenyl)ethylamine, 2-(4-methoxyphenyl)ethylamine, 1-[3-(trifluoromethyl)phenyl]ethylamine, 1-(1-naphthyl)ethylamine, 1-(2-naphthyl)ethylamine, 1-phenylpropylamine, 3-phenylpropylamine, and the like.

In the formulas (I) and (II), when $R^1$ and $R^2$ are taken together with the carbon atom to which $R^1$ and $R^2$ are attached to form an optionally substituted alicyclic hydrocarbon group having 3 to 12 carbon atoms, the number of carbon atoms is preferably 6 to 12. Here, the alicyclic hydrocarbon group having 3 to 12 carbon atoms refers to an alicyclic hydrocarbon group of 3- to 12-membered ring, and "optionally substituted" refers to an optionally substituted alicyclic hydrocarbon group in which hydrogen atoms in a methylene group in the alicyclic hydrocarbon group may be partially or entirely substituted with the other substituent. When substituted with the other substituent, the number of carbon atoms of the substituent is not included in the above-mentioned number of carbon atoms. When $R^1$ and $R^2$ are taken together with the carbon atom to which $R^1$ and $R^2$ are attached to form an optionally substituted alicyclic hydrocarbon group having 3 to 12 carbon atoms, examples of the amine compound (I) include cyclohexylamine, cyclooctylamine, cyclopentylamine, cycloheptylamine, cyclododecylamine, 2-methylcyclohexylamine, 4-methylcyclohexylamine, and the like.

Of the amine compounds (I), cyclohexylamine is preferable. Cyclohexylamine may be obtained by hydrogenating aniline, nitrobenzene, nitrocyclohexane, or the like, or may be obtained by an aminization reaction of cyclohexene or cyclohexanol with ammonia.

It is preferred to use, as an oxygen source of oxygen used for the above-mentioned oxidation, an oxygen-containing gas. This oxygen-containing gas may be either air or pure oxygen, or may be a gas obtained by diluting air or pure oxygen with an inert gas such as nitrogen, argon, or helium. It is also possible to use oxygen enriched air obtained by adding pure oxygen to, air. When using the oxygen-containing gas, the oxygen concentration is preferably 1 to 30% by volume.

The layered silicate may be either a natural product or an artificially synthesized synthetic product, or may be a mixture thereof. Examples of the method for synthesizing a synthetic product include a hydrothermal synthesis reaction method, a solid phase reaction method, a melt synthesis method, and the like. Examples of the layered silicate include smectites such as montmorillonite, saponite, beidellite, nontronite, sauconite, stevensite, hectorite, volkonskoite, and swinefordite; vermiculites; micas such as muscovite, phlogopite, annite, eastonite, siderophyllite tetraferri-annite, polylithionite, celadonite, ferro-celadonite, ferro-aluminoceladonite, aluminoceladonite, tobelite, and paragonite; brittle micas such as clintonite, bityite, and margarite; chlorites such as clinochlore, chamosite, pennantite, nimite, baileychlore, cookeite, and sudoite; talcs; pyrophyllites; kaolinites such as kaolinite, dickite, nacrite, halloysite, amesite, berthierine, cronstedtite, nepouite, kellyite, fraiponite, and brindleyite; serpentines such as antigorite, chrysotile, and lizardite; and the like and, if necessary, two or more layered silicates thereof can also be used. Of these layered silicates, smectite is preferable in view of selectivity of the obtained oxime compound (II). In the present invention, the layered silicate may be used in the form of a clay mineral containing a layered silicate, and examples of the clay mineral containing a layered silicate include clay minerals containing montmorillonite, such as bentonite, activated clay, and activated clay. The layered silicate may be used after calcination, and the temperature of calcination is preferably 150 to 600° C., and the calcination time is preferably 0.1 to 100 hours.

The layered silicate preferably contains cations between layers, and examples of the cation include hydrogen ions, ammonium ions, quaternary ammonium ions, cations of alkali metal elements, cations of alkali earth metal elements, cations of group 3 metal elements, cations of group 4 metal elements, cations of group 5 metal elements, cations of group 6 metal elements, cations of group 7 metal elements, cations of group 8 metal elements, cations of group 9 metal elements, cations of group 10 metal elements, cations of group 11 metal elements, cations of group 12 metal elements, cations of group 13 metal elements, tin ion, lead ion, germanium ion, silicon ion, oxides of positively charged group 4 metal elements, oxides of positively charged group 5 metal elements, oxides of positively charged group 6 metal elements, oxides of positively charged group 7 metal elements, oxides of positively charged group 8 metal elements, oxides of positively charged group 9 metal elements, oxides of positively charged group 10 metal elements, oxides of positively charged group 11 metal elements, oxides of positively charged group 12 metal elements, oxides of positively charged group 13 metal elements, oxides of positively charged tin, oxides of positively charged lead, positively charged germanium oxides, oxides of positively charged silicon, and the like.

Of cations in the layered silicate containing cations between layers, at least one selected from the group consisting of hydrogen ions, ammonium ions, quaternary ammonium ions, cations of group 4 metal elements, cations of group 5 metal elements, cations of group 6 metal elements, germanium ions, oxides of positively charged group 4 metal elements, oxides of positively charged group 5 metal elements, oxides of positively charged group 6 metal elements, and positively charged germanium oxides is preferable; at least one selected from the group consisting of hydrogen ions, ammonium ions, quaternary ammonium ions, cations of group 4 metal elements, germanium ions, oxides of positively charged group 4 metal elements, and positively charged germanium oxides is more preferable; at least one selected from the group consisting of hydrogen ions, cations of group 4 metal elements, germanium ions, oxides of positively charged group 4 metal elements, and positively charged germanium oxides is still more preferable; at least one selected from the group consisting of cations of group 4 metal elements, germanium ions, oxides of positively charged group 4 metal elements, and positively charged germanium oxides are yet more preferable; and at least one selected from the group consisting of cations of group 4 metal elements and oxides of positively charged group 4 metal elements is particularly preferable. Examples of the group 4 metal element include titanium and zirconium. Examples of the group 5 metal element include vanadium, niobium, tantalum, and the like. Examples of the group 6 metal element include chromium, molybdenum, tungsten, and the like. Particularly, when using, as the layered silicate, a layered silicate containing at least one selected from the group consisting of titanium ions, germanium ions, positively charged titanium oxides, and positively charged germanium oxides, the method of the present invention is advantageously employed in view of selectivity of the obtained oxime compound (II).

It is possible to suitably use, as the layered silicate, a layered silicate containing at least one selected from the group consisting of hydrogen ions, ammonium ions, quaternary ammonium ions, cations of group 4 metal elements, cations of group 5 metal elements, cations of group 6 metal elements, germanium ions, oxides of positively charged group 4 metal elements, oxides of positively charged group 5 metal elements, oxides of positively charged group 6 metal elements, and positively charged germanium oxides, and at least one selected from the group consisting of group 8 metal elements, group 9 metal elements, group 10 metal elements, group 11 metal elements, group 12 metal elements, group 13 metal elements, compounds of group 8 metal elements, compounds of group 9 metal elements, compounds of group 10 metal elements, compounds of group 11 metal elements, compounds of group 12 metal elements, compounds of group 13 metal elements, and oxides of positively charged silicon. Of these layered silicates, a layered silicate containing at least one selected from the group consisting of cations of group 4 metal elements, cations of group 5 metal elements, cations of group 6 metal elements, germanium ions, oxides of positively charged group 4 metal elements, oxides of positively charged group 5 metal elements, oxides of positively charged group 6 metal elements, and positively charged germanium oxides and at least one selected from the group consisting of group 8 metal elements, group 9 metal elements, group 10 metal elements, group 11 metal elements, group 12 metal elements, group 13 metal elements, compounds of group 8 metal elements, compounds of group 9 metal elements, compounds of group 10 metal elements, compounds of group 11 metal elements, compounds of group 12 metal elements, compounds of group 13 metal elements, and oxides of positively charged silicon is preferable. Group 8 metal elements, group 9 metal elements, group 10 metal elements, group 11 metal elements, group 12 metal elements, or group 13 metal elements may be contained as cations between layers, or may be supported as a metal simple substance on the layered silicate. Compounds of group 8 metal elements, compounds of group 9 metal elements, compounds of group 10 metal elements, compounds of group 11 metal elements, compounds of group 12 metal elements, or compounds of group 13 metal elements compound may be contained as oxides of positively charged metal element between layers, or may be supported as metal compounds on the layered silicate.

Examples of the group 8 metal element include ruthenium, and the like. Examples of the group 9 metal include iridium, and the like. Examples of the group 10 metal element include nickel, palladium, platinum, and the like. Examples of the group 11 metal elements include silver, gold, and the like. Examples of the group 12 metal element include zinc, and the like. Examples of the group 13 metal elements include aluminum, and the like. At least one selected from the group consisting of the above-mentioned group 8 metal elements, group 9 metal elements, group 10 metal elements, group 11 metal elements, group 12 metal elements, group 13 metal elements, compounds of group 8 metal elements, compounds of group 9 metal elements, compounds of group 10 metal elements, compounds of group 11 metal elements, compounds of group 12 metal elements, compounds of group 13 metal elements, and oxides of positively charged silicon is preferably at least one selected from the group consisting of cations of group 8 metal elements, cations of group 9 metal elements, cations of group 10 metal elements, cations of group 11 metal elements, cations of group 12 metal elements, cations of group 13 metal elements, oxides of positively charged group 8 metal elements, oxides of positively charged group 9 metal elements, oxides of positively charged group 10 metal elements, oxides of positively charged group 11 metal elements, oxides of positively charged group 12 metal elements, oxides of positively charged group 13 metal elements, and oxides of positively charged silicon.

Smectite used suitably in the present invention is a layered compound in which a tetrahedron sheet composed of cation and oxygen, and an octahedron sheet composed of cations and oxygen or hydroxide form a negatively charged monolayer, and cations exist between a monolayer and a monolayer. Generally, it is a layered silicate represented by the following formula (A):

$$X_{0.2\text{-}0.6}(Y^1,Y^2)_{2\text{-}3}Z_4O_{10}(OH)_2 \cdot nH_2O \qquad (A)$$

wherein X represents at least one selected from the group consisting of $K^+$, $Na^+$, $\frac{1}{2}Ca^{2+}$, and $\frac{1}{2}Mg^{2+}$, $Y^1$ represents at least one selected from the group consisting of $Mg^{2+}$, $Fe^{2+}$, $Mn^{2+}$, $Ni^{2+}$, and $Zn2+$, $Y^2$ represents at least one selected from the group consisting of $Li^+$, $Al^{3+}$, $Fe^{3+}$, $Mn^{3+}$, and $Cr^{3+}$, Z represents at least one selected from the group consisting of Si and Al (excluding the case where Z is Al alone), and n≥0. X represents an interlayer cation, $Y^1$ and $Y^2$ represent cations of an octahedron sheet, and Z represents cations of a tetrahedron sheet.

In the present invention, of smectites, montmorillonite, saponite, stevensite, and hectorite are preferably used in view of selectivity of the obtained oxime compound (II).

Montmorillonite used suitably in the present invention is a layered silicate having a 2:1 type structure of silicic acid sheet/aluminic acid sheet/silicic acid sheet as a basic structure of a layer in which the layer is negatively charged by partially substituting aluminum of an aluminic acid sheet with magnesium, and exchangeable cations exist between a layer and a layer, and is generally a layered silicate represented by the following formula (B):

$$X_m(Al_{2-m}Mg_m)Si_4O_{10}(OH)_2 \cdot nH_2O \qquad (B)$$

wherein X represents at least one selected from the group consisting of $K^+$, $Na^+$, $\frac{1}{2}Ca^{2+}$, and $\frac{1}{2}Mg^{2+}$, $0.2 \le m \le 0.6$, and $n \ge 0$. X represents an interlayer cation.

Since the interlayer cation X in smectite or montmorillonite is exchangeable with the other cation, the interlayer cation X is partially or entirely changeable with the other cation by an ion exchange treatment of smectite or montmorillonite. It is preferred to use, as smectite or montmorillonite to be subjected to an ion exchange treatment, those having, as the interlayer cation, at least one selected from the group consisting of sodium ions, potassium ions, and calcium ions. The content of each of sodium ions, potassium ions, and calcium ions in smectite or montmorillonite can be determined by inductively coupled plasma (ICP) emission spectrometry.

It is possible to suitably used, as the layered silicate containing at least one selected from the group consisting of hydrogen ions, ammonium ions, quaternary ammonium ions, cations of group 4 metal elements, cations of group 5 metal elements, cations of group 6 metal elements, germanium ions, oxides of positively charged group 4 metal elements, oxides of positively charged group 5 metal elements, oxides of positively charged group 6 metal elements, and positively charged germanium oxides between layers, which is suitably used in the present invention, those obtained by subjecting a layered silicate having cations between layers to an ion exchange treatment.

Examples of the method in which a layered silicate containing hydrogen ions as interlayer cations include a method in which a layered silicate having cations between layers to subjected to an acid treatment. Examples of an acid used in the acid treatment include inorganic acids such as hydrogen chloride, nitric acid, phosphoric acid, sulfuric acid, and nitrous acid; and organic acids such as acetic acid and trifluoromethanesulfonic acid. Of these acids, the inorganic acid is preferable. Of inorganic acids, hydrogen chloride, nitric acid, and phosphoric acid are preferable. The acid treatment is preferably performed by bringing a layered silicate having exchangeable cations between layers into contact with a solution containing an acid. Interlayer cations are ion-exchanged by the acid treatment, thus enabling the preparation of a layered silicate containing hydrogen ions as the interlayer cation.

The layered silicate containing ammonium ions as the interlayer cation can be prepared by subjecting a layered silicate having cations between layers to ion exchange treatment with at least one selected from the group consisting of ammonia and an ammonium salt. Examples of the ammonium salt include ammonium chloride, ammonium nitrate, ammonium phosphate, ammonium sulfate, ammonium acetate, and the like and, if necessary, two or more ammonium salts thereof can also be used. The ion exchange treatment is preferably performed by bringing a layered silicate having cations between layers into contact with at least one selected from the group consisting of ammonia and an ammonium salt. Interlayer cations X are ion-exchanged by ion exchange treatment, thus enabling the preparation of a layered silicate containing ammonium ions as the interlayer cation.

The layered silicate containing quaternary ammonium ion as the interlayer cation can be prepared, for example, by subjecting a layered silicate having cations between layers to an ion exchange treatment with a quaternary ammonium compound. Examples of the quaternary ammonium compound include hydroxides and halides of various quaternary ammoniums such as tetramethylammonium, tetraethylammonium, n-propyltrimethylammonium, tetra-n-propylammonium, tetra-n-butylammonium, triethylmethylammonium, tri-n-propylmethylammonium, tri-n-butylmethylammonium, benzyltrimethylammonium, and dibenzyldimethylammonium and, if necessary, two or more quaternary ammonium compounds thereof can also be used. The ion exchange treatment is preferably performed by bringing a layered silicate having cations between layers into contact with a solution containing a quaternary ammonium compound. Interlayer cations are ion-exchanged by the ion exchange treatment, thus enabling the preparation of a layered silicate containing quaternary ammonium ions as the interlayer cation.

Examples of the solvent used in the preparation of the above-mentioned solution containing an acid, solution containing at least one selected from the group consisting of ammonia and an ammonium salt, and solution containing a quaternary ammonium compound include polar solvents such as water, methanol, ethanol, acetone, and 1,2-dimethoxyethane and, if necessary, two or more solvents thereof can also be used. Of these solvents, water is preferable. The amount of the solvent used in appropriately set. When the acid treatment is performed, the solution containing an acid preferably has a pH of 3 or lower.

The acid treatment, the ion exchange treatment with at least one selected from the group consisting of ammonia and an ammonium salt, and the ion exchange treatment with a quaternary ammonium compound may be performed in either a batchwise or continuous manner. Examples of the method to be performed in a batchwise manner include, for example, a method in which a layered silicate having cations between layers is immersed in the above-mentioned solution containing an acid, solution containing at least one selected from the group consisting of ammonia and an ammonium salt, or the solution containing a quaternary ammonium compound in a stirring tank, followed by mixing with stirring. Examples of the method to be performed in a continuous manner include, for example, a method in which the above-mentioned solution containing an acid, the solution containing at least one selected from the group consisting of ammonia and an ammonium salt, or solution containing a quaternary ammonium compound is allowed to flow through a tubular container filled with a layered silicate having cations between layers; a method in which a solution phase of a mixture is withdrawn while feeding the above-mentioned solution containing an acid, the solution containing at least one selected from the group consisting of ammonia and an ammonium salt, or the solution containing a quaternary ammonium compound into a stirring tank charged with a layered silicate having cations between layers; and the like.

The temperature in the above-mentioned acid treatment, or the ion exchange treatment with at least one selected from the group consisting of ammonia and an ammonium salt, or the ion exchange treatment with a quaternary ammonium compound is usually 0 to 150° C., and preferably 20 to 100° C. The time in these treatments is usually 0.1 to 240 hours, and preferably 0.5 to 120 hours. The pressure in these treatments is usually absolute pressure of 0.1 to 1 MPa, and preferably atmospheric pressure. The use amount of the above-mentioned solution containing an acid, the solution containing at least one selected from the group consisting of ammonia and an ammonium salt, or the solution containing a quaternary ammonium compound is appropriately set based on the layered silicate having cations between layers. The above-mentioned acid treatment, or the ion exchange treatment with at least one selected from the group consisting of ammonia and an ammonium salt, or the ion exchange treatment with a quaternary ammonium compound may be performed a plurality of times, and these treatment may also be used in combination.

The layered silicate containing, as the interlayer cation, at least one cation selected from the group consisting of cations of group 4 metal elements, cations of group 5 metal elements, cations of group 6 metal elements, and germanium ions can be prepared, for example, by subjecting a layered silicate having cations between layers to an ion exchange treatment [hereinafter, the ion exchange treatment is sometimes referred to as an ion exchange treatment with a metal element compound] with at least one compound selected from the group consisting of compounds of group 4 metal elements, compounds of group 5 metal elements, compounds of group 6 metal elements, and germanium compounds. The ion exchange treatment is preferably performed by bringing a layered silicate having cations between layers into contact with a solution containing at least one compound selected from the group consisting of compounds of group 4 metal elements, compounds of group 5 metal elements, compounds of group 6 metal elements, and germanium compounds. Interlayer cations are ion-exchanged by the ion exchange treatment, thus enabling the preparation of a layered silicate containing, as the interlayer cation, at least one cation selected from the group consisting of cations of group 4 metal elements, cations of group 5 metal elements, cations of group 6 metal elements, and germanium ions. The content of at least one cation selected from the group consisting of cations of group 4 metal elements, cations of group 5 metal elements, cations of group 6 metal elements, and germanium ions in the layered silicate is preferably 0.01 to 50% by weight, more preferably 0.1 to 25% by weight, and still more preferably 0.2 to 10% by weight. When two or more cations selected from the group consisting of cations of group 4 metal elements, cations of group 5 metal elements, cations of group 6 metal elements, and germanium ions is contained in the layered silicate, the total content thereof may be within the above range. The content of each of cations of group 4 metal elements, cations of group 5 metal elements, cations of group 6 metal elements, and germanium ions can be determined, for example, by inductively coupled plasma (ICP) emission spectrometry.

Examples of the compound of group 4 metal elements include inorganic compounds of group 4 metal elements and organic compounds of group 4 metal elements. Examples of the inorganic compound of group 4 metal elements include halides of group 4 metal elements, such as titanium trichloride ($TiCl_3$), titanium tetrachloride ($TiCl_4$), titanium tetrabromide ($TiBr_4$), titanium tetrafluoride ($TiF_4$), titanium tetraiodide ($TiI_4$), zirconium trichloride ($ZrCl_3$), zirconium tetrachloride ($ZrCl_4$), zirconium tribromide ($ZrBr_3$), zirconium tetrabromide ($ZrBr_4$), zirconium tetrafluoride ($ZrF_4$), and zirconium tetraiodide ($ZrI_4$); nitrates of group 4 metal elements, such as titanium tetranitrate ($Ti(NO_3)_4$) and zirconium tetranitrate ($Zr(NO_3)_4$); oxynitates of group 4 metal elements, such as zirconyl nitrate ($ZrO(NO_3)_2$); sulfates of group 4 metal elements, such as titanium disulfate ($Ti(SO_4)_2$) and zirconium disulfate ($Zr(SO_4)_2$); phosphates of group 4 metal elements, such as titanium phosphate ($Ti_3(PO_4)_4$) and zirconium phosphate ($Zr_3(PO_4)_4$); and the like. Examples of the organic compound of group 4 metal elements include alkoxide compounds of group 4 metal elements, such as $Ti(OR^3)_4$ (hereinafter, $R^3$ represents an alkyl group having 1 to 4 carbon atoms) and $Zr(OR^3)_4$; halogenated alkoxide compounds of group 4 metal elements, such as $TiCl(OR^3)_3$, $TiCl_2(OR^3)_2$, $TiCl_3(OR^3)$, $ZrCl(OR^3)_3$, $ZrCl_2(OR^3)_2$, and $ZrCl_3(OR^3)$; acetates of group 4 metal elements, such as titanium tetraacetate ($Ti(CH_3COO)_4$) and zirconium tetraacetate ($Zr(CH_3COO)_4$); and the like. Hydrates of these exemplified compounds may also be used as compounds of group 4 metal elements. Two or more compounds of group 4 metal elements may also be used. Compounds of group 4 metal elements are preferably halides of group 4 metal elements, sulfates of group 4 metal elements, alkoxide compounds of group 4 metal elements, or oxynitrates of group 4 metal elements, and more preferably halides of group 4 metal elements.

Examples of the compound of group 5 metal elements include inorganic compounds of group 5 metal elements, and organic compounds of group 5 metal elements. Examples of the inorganic compound of group 5 metal elements include halides of group 5 metal elements, such as vanadium trichloride ($VCl_3$), vanadium tetrachloride ($VCl_4$), vanadium tribromide ($VBr_3$), vanadium trifluoride ($VF_3$), vanadium tetrafluoride ($VF_4$), vanadium triiodide ($VI_3$), niobium trichloride ($NbCl_3$), niobium tetrachloride ($NbCl_5$), niobium tribromide ($NbBr_3$), niobium pentabromide ($NbBr_5$), niobium pentafluoride ($NbF_5$), niobium pentaiodide ($NbI_5$), tantalum trichloride ($TaCl_3$), tantalum pentachloride ($TaCl_5$), tantalum pentabromide ($TaBr_5$), tantalum pentafluoride ($TaF_5$), and tantalum pentaiodide ($TaI_5$). Examples of the organic compound of group 5 metal elements include alkoxide compounds of group 5 metal elements, such as $Nb(OR^3)_5$ and $Ta(OR^3)_5$. Hydrates of these exemplified compounds may also be used as compounds of group 5 metal elements. Two or more compounds of group 5 metal elements may also be used.

Examples of the compound of group 6 metal elements include inorganic compounds of group 6 metal elements and organic compounds of group 6 metal elements. Examples of the inorganic compound of group 6 metal elements include halides of group 6 metal elements, such as chromium dichloride ($CrCl_2$), chromium trichloride ($CrCl_3$), chromium dibromide ($CrBr_2$), chromium tribromide ($CrBr_3$), chromium difluoride ($CrF_2$), chromium trifluoride ($CrF_3$), chromium diiodide ($CrI_2$), chromium triiodide ($CrI_3$), molybdenum trichloride ($MoCl_3$), molybdenum pentachloride ($MoCl_5$), molybdenum tribromide ($MoBr_3$), molybdenum tetrafluoride ($MoF_4$), molybdenum hexafluoride ($MoF_6$), tungsten tetrachloride ($WCl_4$), tungsten hexachloride ($WCl_6$), tungsten pentabromide ($WBr_5$), and tungsten hexafluoride ($WF_6$); nitrates of group 6 metal elements, such as chromium trinitrate ($Cr(NO_3)_3$); sulfates of group 6 metal elements, such as chromium(III) sulfate ($Cr_2(SO_4)_3$); and the like. Examples of the organic compound of group 6 metal elements include alkoxide compounds of group 6 metal elements, such as $Mo(OR^3)_5$, $W(OR^3)_5$, and $W(OR^3)_6$; acetates of group 6 metal elements, such as chromium triacetate ($Cr(CH_3COO)_3$); and the like. Hydrates of these exemplified compounds may also be used as compounds of group 6 metal elements. Two or more compounds of group 6 metal elements may also be used.

Examples of the germanium compound include inorganic compounds of germanium and organic compounds of germanium. Examples of the inorganic compound of germanium include halides of germanium, such as germanium tetrachloride ($GeCl_4$), germanium tetrabromide ($GeBr_4$), germanium tetrafluoride ($GeF_4$), and germanium tetraiodide ($GeI_4$); sulfides of germanium, such as germanium sulfide (GeS); and the like. Examples of the organic compound of germanium include alkoxide compounds of germanium, such as $Ge(OR^3)_4$; halogenated alkoxide compounds of germanium, such as $GeCl(OR^3)_3$, $GeCl_2(OR^3)_2$, and $GeCl_3(OR^3)$; and the like. Hydrates of these exemplified compounds may also be used as germanium compounds. Two or more germanium compounds may also be used. Of germanium compounds, halides of germanium and alkoxide compounds of germanium are preferable.

In the above-mentioned ion exchange treatment with a metal element compound, the use amount of at least one compound selected from the group consisting of compounds of group 4 metal elements, compounds of group 5 metal elements, compounds of group 6 metal elements, and germanium compounds is preferably 0.01 to 100 parts by weight, and more preferably 0.05 to 50 parts by weight, based on 100 parts by weight of a layered silicate having cations between layers in terms of metal elements contained in at least one compound selected from the group consisting of compounds of group 4 metal elements, compounds of group 5 metal elements, compounds of group 6 metal elements, and germanium compounds. When using two or more compounds selected from the group consisting of compounds of group 4 metal elements, compounds of group 5 metal elements, compounds of group 6 metal elements, and germanium compounds, the total use amount thereof may be within the above range.

When the above-mentioned ion exchange treatment with a metal element compound is performed by bringing a layered silicate having cations between layers into contact with a solution containing at least one compound selected from the group consisting of compounds of group 4 metal elements, compounds of group 5 metal elements, compounds of group 6 metal elements, and germanium compounds, examples of the solvent used in the preparation of the solution include polar solvents such as water, methanol, ethanol, acetone, and 1,2-dimethoxyethane and, if necessary, two or more solvents thereof can also be used. The solution may be acidic, basic, or neutral, and it is preferred to use an aqueous acidic solution containing at least one compound selected from the group consisting of compounds of group 4 metal elements, compounds of group 5 metal elements, compounds of group 6 metal elements, and germanium compounds. If an aqueous solution prepared by mixing at least one compound selected from the group consisting of compounds of group 4 metal elements, compounds of group 5 metal elements, compounds of group 6 metal elements, and germanium compounds with water has an acidic pH, the solution thus obtained may be used as it is as the aqueous acidic solution, or may be used after mixing with an acid. If an aqueous solution prepared by mixing at least one compound selected from the group consisting of compounds of group 4 metal elements, compounds of group 5 metal elements, compounds of group 6 metal elements, and germanium compounds with water has not an acidic pH, an aqueous acidic solution obtained by mixing with an acid may be used.

Examples of the acid to be optionally used for the preparation of the aqueous acidic solution include an organic acid and an inorganic acid. Of these acids, an inorganic acid is preferable. Examples of the inorganic acid include hydrogen chloride, sulfuric acid, phosphoric acid, nitric acid, and the like. Of these inorganic acids, hydrogen chloride is preferable. The pH of the aqueous acidic solution is preferably 4 or lower. The aqueous acidic solution may also contain a polar organic solvent such as methanol, ethanol, acetone, or 1,2-dimethoxyethane. When using, as at least one compound selected from the group consisting of, compounds of group 4 metal elements, compounds of group 5 metal elements, compounds of group 6 metal elements, and germanium compounds, compounds such as a hydrolyzable halide, an alkoxide compound, and oxynitrate in the preparation of the aqueous acidic solution, the compound is hydrolyzed to form an oxide, thus enabling the preparation of a layered silicate in which interlayer cations are ion-exchanged with at least one selected from the group consisting of oxides of positively charged group 4 metal elements, oxides of positively charged group 5 metal elements, oxides of positively charged group 6 metal elements, and positively charged germanium oxides. When group 4 metal elements contained in two or more compounds of compounds such as hydrolysable halides of two or more group 4 metal elements, alkoxide compounds, or oxynitrate, compounds such as hydrolyzable halides of two or more group 5 metal elements, alkoxide compounds, or oxynitrate, or compounds such as hydrolysable halides of two or more group 6 metal elements, alkoxide compounds, or oxynitrate are not identical in the respective compounds, it is also possible to forma complex oxide containing, as constituent elements, two or more group 4 metal elements, two or more group 5 metal elements, or two or more group 6 metal elements, thus enabling the introduction of a positively charged complex oxide containing, as interlayer cations, constituent elements such as two or more group 4 metal elements, two or more group 5 metal elements, or two or more group 6 metal elements. When using two or more compounds selected from the group consisting of compounds of group 4 metal elements, compounds of group 5 metal elements, compounds of group 6 metal elements, and germanium compounds, it is possible to introduce a positively charged complex oxide containing, as interlayer cations, constituent elements such as two or more metal elements selected from the group consisting of group 4 metal elements, group 5 metal elements, group 6 metal elements, and germanium.

A solution containing at least one compound selected from the group consisting of compounds of group 4 metal elements, compounds of group 5 metal elements, compounds of group 6 metal elements, and germanium compounds may also contain compounds of the below-mentioned elements, in addition to compounds of group 4 metal elements, compounds of group 5 metal elements, compounds of group 6 metal elements, and germanium compound. Before and/or after bringing the solution into contact with the layered silicate, contact with a solution containing compounds of the below-mentioned elements may also be performed. Examples of elements other than group 4 metal elements, group 5 metal elements, group 6 metal elements, and germanium compounds (hereinafter sometimes referred to as the other element) include compounds of alkali metal elements, compounds of alkali earth metals of group 3 metal elements, compounds of alkali earth metals of group 7 metal elements, compounds of group 8 metal elements, compounds of group 9 metal elements, compounds of group 10 metal elements, compounds of group 11 metal elements, compounds of group 12 metal elements, compounds of group 13 metal elements, tin compounds, lead compounds, silicon compounds, arsenic compounds, antimony compounds, bismuth compounds, selenium compounds, tellurium compounds, and the like and, if necessary, two or more compounds thereof can also be used. Of these compounds, compounds of group 8 metal elements, compounds of group 9 metal elements, compounds of group 10 metal elements, compounds of group 11 metal elements, compounds of group 12 metal elements, compounds of group 13 metal elements, and silicon compounds are preferable. When a compound hydrolyzed under acidic condition, such as an alkoxide compound is used as compounds of these elements, and a solution containing at least one compound selected from the group consisting of compounds of group 4 metal elements, compounds of group 5 metal elements, compounds of group 6 metal elements, and germanium compounds, and compounds of the other element is an aqueous acidic solution, it is possible to prepare a layered silicate in which interlayer cations of the obtained layered silicate is ion-exchanged with the following i), ii) and/or iii).

i) a mixture of cations of at least one metal element selected from the group consisting of group 4 metal elements, group 5 metal elements, group 6 metal elements, and germanium, with positively charged oxides of the other element;

ii) a mixture of at least one selected from the group consisting of oxides of positively charged group 4 metal elements, oxides of positively charged group 5 metal elements, oxides of positively charged group 6 metal elements, and positively charged germanium oxides, with positively charged oxides of the other element, when at least one compound selected from the group consisting of compounds of group 4 metal elements, compounds of group 5 metal elements, compounds of group 6 metal elements, and germanium compounds is a compound hydrolyzed under acidic condition, and iii) a positively charged complex oxide containing, as constituent elements, at least one metal element selected from the group consisting of group 4 metal elements, group 5 metal elements, group 6 metal elements, and germanium, and the other element.

The compound containing the other element hydrolyzed under acidic condition includes, for example, a silicon alkoxide compound, and examples of the silicon alkoxide compound include tetraalkyl orthosilicates such as tetramethyl orthosilicate, tetraethyl orthosilicate, tetrapropyl orthosilicate, and tetrabutyl orthosilicate. Use of the silicon alkoxide compound enables the preparation of a layered silicate containing oxides of positively charged silicon.

The above-mentioned ion exchange treatment with a metal element compound may be performed in either a batchwise or continuous manner. Examples of the method performed in a batchwise manner method include, for example, a method in which a layered silicate having cations between layers is immersed in a solution containing at least one compound selected from the group consisting of compounds of group 4 metal elements, compounds of group 5 metal elements, compounds of group 6 metal elements, and germanium compounds in a stirring tank, followed by mixing with stirring. Examples of the method performed in a batchwise manner method include, for example, a method in which a solution containing at least one compound selected from the group consisting of compounds of group 4 metal elements, compounds of group 5 metal elements, compounds of group 6 metal elements, and germanium compounds is allowed to flow through a tubular container filled with a layered silicate having cations between layers; a method in which a liquid phase of a mixture is withdrawn while feeding a solution containing at least one compound selected from the group consisting of compounds of group 4 metal elements, compounds of group 5 metal elements, compounds of group 6 metal elements, and germanium compounds into a stirring tank charged with a layered silicate having cations between layers; and the like.

The temperature of the above-mentioned ion exchange treatment with a metal element compound is usually 0 to 150° C., preferably 10 to 100° C., and more preferably 30 to 70° C. The time of the ion exchange treatment is usually 0.1 to 240 hours, and preferably 0.5 to 120 hours. The time of the ion exchange treatment is usually absolute pressure of 0.1 to 1 MPa, and preferably atmospheric pressure. The use amount of a solution containing at least one compound selected from the group consisting of compounds of group 4 metal elements, compounds of group 5 metal elements, compounds of group 6 metal elements, and germanium compounds is appropriately set based on the layered silicate having exchangeable cations between layers. The above-mentioned ion exchange treatment with a metal element compound may be performed a plurality of times, if necessary. It is also possible to use in combination with at least one treatment selected from the group consisting of the above-mentioned acid treatment, the above-mentioned ion exchange treatment with at least one selected from the group consisting of ammonia and an ammonium salt, and the above-mentioned ion exchange treatment with a quaternary ammonium compound. It is possible to prepare a layered silicate containing at least one selected from the group consisting of hydrogen ions, ammonium ions, quaternary ammonium ions, cations of group 4 metal elements, cations of group 5 metal elements, cations of group 6 metal elements, germanium ions, oxides of positively charged group 4 metal elements, oxides of positively charged group 5 metal elements, oxides of positively charged group 6 metal elements, and positively charged germanium oxides by performing at least one treatment selected from the group consisting of the above-mentioned ion exchange treatment with a metal element compound, the above-mentioned acid treatment, the above-mentioned ion exchange treatment with at least one selected from the group consisting of ammonia and an ammonium salt, and the above-mentioned ion exchange treatment with a quaternary ammonium compound.

It is also possible to subject a layered silicate containing, as the interlayer cation, at least one cation selected from the group consisting of cations of group 4 metal elements, cations of group 5 metal elements, cations of group 6 metal elements, and germanium ion to a contact treatment with the above-mentioned solution containing compounds of the other element. Such contact treatment enables supporting of at least one selected from the group consisting of the other element and compounds of the other element, or the introduction of at least one selected from the group consisting of cations of the other element and oxides of positively charged other element between layers.

The layered silicate obtained, after performing at least one treatment selected from the group consisting of the above-mentioned ion exchange treatment with a metal element compound, the above-mentioned acid treatment, the above-mentioned ion exchange treatment with at least one selected from the group consisting of ammonia and an ammonium salt, and the above-mentioned ion exchange treatment with a quaternary ammonium compound, is subjected to a treatment such as washing or drying, if necessary. If the layered silicate obtained after the treatment is in a slurry state, the layered silicate may be recovered by drying the slurry, or the layered silicate may be recovered by separation with filtration or decantation, followed by washing and further drying, if necessary. It is preferred that the layered silicate obtained after the treatment is subjected to washing since a layered silicate exhibiting high catalytic activity is obtained. Drying can be performed under either a normal pressure or reduced pressure, and the drying temperature is preferably 20 to 250° C., and the drying time is preferably 0.5 to 100 hours. Drying may be performed in an atmosphere of an oxygen-containing gas such as air, or an atmosphere of an inert gas such as nitrogen, helium, argon, or carbon dioxide.

After drying, calcination may be performed, if necessary. The calcination temperature is preferably 150 to 600° C., and the calcination time is preferably 0.1 to 100 hours.

Calcination may be performed in an atmosphere of an oxygen-containing gas such as air, or an atmosphere of an inert gas such as nitrogen, helium, argon, or carbon dioxide. The oxygen-containing gas and inert gas may contain steam. Calcination may be performed in a multi-stage in an atmosphere of an oxygen-containing gas or an inert gas. Calcination may be performed in a fluidized bed type or fixed bed type. The device used in calcination is not particularly limited as long as it is a device capable of heating, and it is possible to use, for example, a hot air circulation calcination furnace, a stationary type calcination furnace, a tunnel furnace, a rotary kiln, a far infrared furnace, a microwave heating furnace, and the like.

The layered silicate used for oxidization may be used after molding, using a binder, or by supporting on a carrier, if necessary. Such molding treatment or supporting treatment may be performed before or after the ion exchange treatment. The molding treatment can be performed, for example, by a method such as extrusion, compression, tableting, fluidization, rolling, or spraying, and it is possible to mold into a desired shape, for example, granule, pellet, sphere, cylinder, plate, ring, clover, or the like.

It is preferred to use a solvent in the oxidation. Examples of the solvent include an organic solvent, water, and a mixed solvent of an organic solvent and water. Of these solvents, an organic solvent or a mixed solvent of an organic solvent and water is preferable, and an organic solvent is more preferable. Examples of the organic solvent include alcohols such as methanol, ethanol, propanol, isopropanol, n-butanol, t-butanol, n-hexanol, 2-ethylhexanol, and n-dodecanol; aliphatic hydrocarbons such as pentane, hexane, heptane, octane, petroleum ether, and ligroin; alicyclic hydrocarbons such as cyclopentane, cyclohexane, and methylcyclohexane; aromatic hydrocarbon such as benzene, toluene, o-xylene, m-xylene, and p-xylene; halogenated hydrocarbons such as dichloromethane, chloroform, 1,2-dichloroethane, 1,1,1-trichloroethane, 1,1,2-trichloroethylene, 1,1,2,2-tetrachloroethylene, chlorobenzene, and o-dichlorobenzene; nitriles such as acetonitrile and benzonitrile; nitro compounds such as nitrobenzene; ester compounds such as ethyl acetate, isopropyl acetate, butyl acetate, and ethyl benzoate; and the like, and it is also possible to use two or more solvents thereof, if necessary. Of these solvents, alcohol, aromatic hydrocarbon, and nitrile are preferable. Of these alcohols, methanol, ethanol, and t-butanol are preferable. Of these aromatic hydrocarbons, toluene, o-xylene, m-xylene, and p-xylene are preferable. Of these nitriles, acetonitrile is preferable.

When using the solvent, the amount is usually 0.1 to 300 parts by weight, and preferably 0.5 to 100 parts by weight, based on 1 part by weight of the amine compound (I).

Oxidation may be performed in a batchwise manner, a semi-batchwise manner, a continuous manner, or a combination of a batchwise manner, a semi-batchwise manner, and a continuous manner. When oxidation is performed in a continuous manner, oxidation can be carried out by various manners such as extraction of a liquid phase of the reaction mixture while feeding a reaction starting material into a fixed bed type, fluidized bed type, moving bed type, suspension type, stirring/mixing type, or loop type reactor.

The reaction temperature in the oxidation is preferably 50 to 200° C., and more preferably 70 to 150° C. The reaction pressure is usually absolute pressure of 0.1 to 10 MPa, and preferably 0.2 to 7.0 MPa. The oxidation is preferably performed under pressure. In this case, the pressure may be adjusted using an inert gas such as nitrogen or helium. When the oxidation is carried out in a stirring/mixing type reactor under liquid phase in a batchwise or continuous manner using an oxygen-containing gas, an oxygen-containing gas may be fed to a vapor phase portion of a reactor, or an oxygen-containing gas may be fed in a liquid phase, or an oxygen-containing gas may be fed in a vapor phase portion and a liquid phase of a reactor.

In the oxidation, a radical initiator, a phenol-based chain transfer agent, and the like may be allowed to coexist. From the viewpoint of an improvement in selectivity of the oxime compound (II), it is preferred that a radical initiator is allowed to coexist. Examples of the radical initiator include a hydrazyl radical and a hydrazine compound disclosed in WO 2005/009613 A, and an azo compound and oxide disclosed in JP 2005-15381 A, and two or more radical initiators may be used, if necessary. The hydrazyl radical is preferably 2,2-diphenyl-1-picrylhydrazyl or 2,2-di(4-tert-octylphenyl)-1-picrylhydrazyl. The hydrazine compound is preferably 1,1-diphenyl-2-picrylhydrazine. In the present invention, at least one selected from the group consisting of 2,2-diphenyl-1-picrylhydrazyl and 1,1-diphenyl-2-picrylhydrazine is preferably used as the radical initiator. Examples of the phenol-based chain transfer agent include compounds disclosed in JP 2005-15382 A.

Post treatment operations of the reaction mixture containing the oxime compound (II) obtained by the oxidation can be appropriately selected, and the oxime compound (II) can be used for various applications after purifying using treatments such as filtration, washing, distillation, crystallization, extraction, recrystallization, and chromatography in combination. A catalyst recovered after the oxidation can be reduced after subjecting to treatments such as washing, calcination, and ion exchange treatment, if necessary. When the reaction mixture contains a solvent and an unreacted material, the solvent and unreacted material recovered can be reused.

The oxime compound (II) thus obtained is suitably used as a starting material for the production of the amide compound (III) after allowing to undergo the Beckmann rearrangement reaction.

When, in the oxime compound (II), $R^1$ and $R^2$ are taken together with the carbon atom to which $R^1$ and $R^2$ are attached to form an optionally substituted alicyclic hydrocarbon group having 3 to 12 carbon atoms, the amide compound (III) obtained by the Beckmann rearrangement reaction of the oxime compound (II), $R^1$ and $R^2$ are taken together with the nitrogen atom to which $R^1$ is attached and the carbon atom to which $R^2$ is attached to form an optionally substituted having 3 to 12 carbon atoms aliphatic heterocycle.

Examples of such Beckmann rearrangement reaction include a method which is performed under liquid phase condition, and a method which is performed under vapor phase condition. Examples of the Beckmann rearrangement reaction under liquid phase condition include, for example, a method which is performed in the presence of strong acid such as fuming sulfuric acid, and can be performed in accordance with the method mentioned in JP 48-4791 A. Examples of the Beckmann rearrangement reaction under vapor phase condition include, for example, a method which is performed in the presence of a solid catalyst such as zeolite, and can be performed in accordance with the method mentioned in JP 5-170732 A. For example, when using cyclohexylamine as the amine compound (I), ε-caprolactam can be produced by the Beckmann rearrangement reaction of cyclohexanone oxime obtained by the oxidation.

EXAMPLES

The present invention will be described by way of the following Examples and Comparative Examples, but it is not construed to limit the present invention thereto. In the following Examples, cyclohexylamine [compound in which $R^1$ and $R^2$ are taken together with the carbon atom to which $R^1$ and $R^2$ are attached to form a cyclohexane ring in the formula (I)] and cyclohexanone oxime [compound in which $R^1$ and $R^2$ are taken together with the carbon atom to which $R^1$ and $R^2$ are attached to form a cyclohexane ring in the formula (II)] in the reaction solution were analyzed by gas chromatography, and the conversion ratio of cyclohexylamine as well as the selectivity of cyclohexanone oxime were calculated based on the results of the analysis.

Reference Example 1

Preparation of Catalyst

In a 2 L poly beaker, 687 g of 1,2-dimethoxyethane (manufactured by Wako Pure Chemical Industries, Ltd.) and 13.24 g of 35% by weight hydrochloric acid (manufactured by Wako Pure Chemical Industries, Ltd.) were charged, and 15 g of montmorillonite (Kunipia F, manufactured by KUNIMINE INDUSTRIES CO., LTD., montmorillonite containing sodium ions, potassium ions, and calcium ions as interlayer cations) was added while stirring the obtained mixture. After stirring at room temperature for 5 minutes, a vapor phase portion in the poly beaker was replaced by nitrogen. Using a water bath, the temperature was raised to 50° C. while stirring the mixture in the poly beaker, 17.97 g of a 20% by weight titanium trichloride solution (dilute hydrochloric acid solution of $TiCl_3$, manufactured by Wako Pure Chemical Industries, Ltd.) was added dropwise over 1 hour. After completion of the dropwise addition, stirring was continued at 50° C. for 6 hours. After 6 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. to prepare a catalyst A (montmorillonite containing titanium ions between layers).

Example 1

In a reactor made of SUS316 (volume: 200 mL) equipped with a thermocouple, a magnetic stirrer, a gas feed line, and a gas discharge line, 0.30 g of the catalyst A obtained in Reference Example 1, 1.52 g (15.3 mmol) of cyclohexylamine (manufactured by Wako Pure Chemical Industries, Ltd.), and 7.07 g of acetonitrile (manufactured by Wako Pure Chemical Industries, Ltd.) were charged and a vapor phase portion in the reactor was replaced by nitrogen. After the reactor was sealed, a mixed gas of oxygen and nitrogen (oxygen concentration: 7% by volume) was introduced into the vapor phase portion in the reactor to thereby adjust the pressure in the reactor to 0.90 MPa (gauge pressure). Next, the temperature in the reactor was raised to 80° C. while stirring. The pressure in the reactor was 1.05 MPa (gauge pressure). After keeping the reactor warm at 80° C. for 4 hours while continuing to stir, cooling was performed. The obtained reaction mixture was diluted by the addition of methanol and filtrated, and then the obtained filtrate was analyzed. As a result, the conversion ratio of cyclohexylamine was 0.9% and the selectivity of cyclohexanone oxime was 84.6%.

Example 2

The same operation as in Example 1 was performed, except that temperature rise to 80° C. was replaced by temperature rise to 90° C. and the reactor kept warm at 90° C. for 4 hours. The pressure in the reactor was 1.10 MPa (gauge pressure) when the temperature was raised to 90° C. The obtained filtrate was analyzed. As a result, the conversion ratio of cyclohexylamine was 2.3% and the selectivity of cyclohexanone oxime was 80.3%.

Example 3

The same operation as in Example 1 was performed, except that 0.14 g (0.36 mmol) of 2,2-diphenyl-1-picrylhydrazyl (manufactured by Aldrich) was charged in the reactor, in addition to the catalyst A, cyclohexylamine, and acetonitrile. The obtained filtrate was analyzed. As a result, the conversion ratio of cyclohexylamine was 19.8% and the selectivity of cyclohexanone oxime was 91.8%.

Example 4

The same operation as in Example 3 was performed, except that the use amount of 2,2-diphenyl-1-picrylhydrazyl was changed from 0.14 g to 0.014 g (0.036 mmol). The obtained filtrate was analyzed. As a result, the conversion ratio of cyclohexylamine was 2.1% and the selectivity of cyclohexanone oxime was 86.5%.

Example 5

The same operation as in Example 3 was performed, except that 7.03 g of t-butanol (manufactured by Wako Pure Chemical Industries, Ltd., water content: 2,000 ppm by weight) was used in place of 7.07 g of acetonitrile. The obtained filtrate was analyzed. As a result, the conversion ratio of cyclohexylamine was 9.6% and the selectivity of cyclohexanone oxime was 94.5%.

Example 6

The same operation as in Example 3 was performed, except that 7.05 g of toluene (manufactured by Wako Pure Chemical Industries, Ltd.) was used in place of 7.07 g of acetonitrile. The obtained filtrate was analyzed. As a result, the conversion ratio of cyclohexylamine was 14.3% and the selectivity of cyclohexanone oxime was 88.6%.

Example 7

The same operation as in Example 3 was performed, except that 7.04 g of a mixed solution of t-butanol and water [t-butanol/water=7/1 (weight ratio)] was used in place of 7.07 g of acetonitrile. The obtained filtrate was analyzed. As a result, the conversion ratio of cyclohexylamine was 2.2% and the selectivity of cyclohexanone oxime was 87.8%.

Example 8

The same operation as in Example 3 was performed, except that 7.14 g of methanol (manufactured by Wako Pure Chemical Industries, Ltd., water content: 1,000 ppm by weight) was used in place of 7.07 g of acetonitrile. The obtained filtrate was analyzed. As a result, the conversion ratio of cyclohexylamine was 7.2% and the selectivity of cyclohexanone oxime was 86.9%.

Example 9

The same operation as in Example 3 was performed, except that 0.31 g of montmorillonite KSF (manufactured by Aldrich) was used in place of 0.30 g of the catalyst A. The obtained filtrate was analyzed. As a result, the conversion ratio of cyclohexylamine was 9.5% and the selectivity of cyclohexanone oxime was 59.3%.

Example 10

The same operation as in Example 3 was performed, except that 0.30 g of activated clay (manufactured by Sigma-Aldrich Japan K.K.) was used in place of 0.30 g of the catalyst A. The obtained filtrate was analyzed. As a result, the conversion ratio of cyclohexylamine was 7.4% and the selectivity of cyclohexanone oxime was 57.3%.

Reference Example 2

Preparation of Catalyst

The same operation as in Reference Example 1 was performed, except that 36.18 g of a 20% by weight titanium trichloride solution was used in place of 17.97 g of the 20% by weight titanium trichloride solution, a catalyst B (montmorillonite containing titanium ions between layers) was prepared.

Example 11

The same operation as in Example 1 was performed, except that 0.30 g of the catalyst B obtained in Reference Example 2 was used in place of 0.30 g of the catalyst A. The obtained filtrate was analyzed. As a result, the conversion ratio of cyclohexylamine was 1.2% and the selectivity of cyclohexanone oxime was 77.0%.

Reference Example 3

Preparation of Catalyst

The same operation as in Reference Example 1 was performed, except that 72.76 g of a 20% by weight titanium trichloride solution was used in place of 17.97 g of the 20% by weight titanium trichloride solution, a catalyst C (montmorillonite containing titanium ions between layers) was prepared.

Example 12

The same operation as in Example 1 was performed, except that 0.60 g of the catalyst C obtained in Reference Example 3 was used in place of 0.30 g of the catalyst A. The obtained filtrate was analyzed. As a result, the conversion ratio of cyclohexylamine was 2.7% and the selectivity of cyclohexanone oxime was 78.0%.

Reference Example 4

Preparation of Catalyst

In a 1 L separable flask, 600 g of 2 mol/L hydrochloric acid (manufactured by Wako Pure Chemical Industries, Ltd.) and 60 g of montmorillonite (Kunipia F, manufactured by KUNIMINE INDUSTRIES CO., LTD., montmorillonite containing sodium ions, potassium ions, and calcium ions as interlayer cations) were charged, followed by stirring at room temperature for 5 minutes stirring. Using an oil bath, the temperature was raised to 90° C. while stirring the mixture in the separable flask, and stirring was continued at 90° C. for 12 hours. After 12 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. to prepare a catalyst D (montmorillonite containing hydrogen ions between layers).

Example 13

The same operation as in Example 3 was performed, except that 0.30 g of the catalyst D obtained in Reference Example 4 was used in place of 0.30 g of the catalyst A. The obtained filtrate was analyzed. As a result, the conversion ratio of cyclohexylamine was 6.7% and the selectivity of cyclohexanone oxime was 65.1%.

Reference Example 5

Preparation of Catalyst

In a 2 L poly beaker, 700 g of 1,2-dimethoxyethane (manufactured by Wako Pure Chemical Industries, Ltd.) was charged and 1.71 g of a 20% by weight titanium trichloride solution (dilute hydrochloric acid solution of $TiCl_3$, manufactured by Wako Pure Chemical Industries, Ltd.) was added while stirring, followed by stirring at room temperature for 5 minutes stirring. To the obtained mixed solution, 15 g of montmorillonite (Kunipia F, manufactured by KUNIMINE INDUSTRIES CO., LTD., montmorillonite containing sodium ions, potassium ions, and calcium ions as interlayer cations) was added. After stirring at room temperature for 5 minutes, a vapor phase portion in the poly beaker was replaced by nitrogen. Using a water bath, the temperature was raised to 50° C. while stirring the mixture in the poly beaker, and stirring was continued at 50° C. for 6 hours. After 6 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. to prepare a catalyst E (montmorillonite containing titanium ions between layers).

Example 14

The same operation as in Example 3 was performed, except that 0.30 g of the catalyst E obtained in Reference Example 5 was used in place of 0.30 g of the catalyst A. The obtained filtrate was analyzed. As a result, the conversion ratio of cyclohexylamine was 19.8% and the selectivity of cyclohexanone oxime was 88.1%.

Reference Example 6

Preparation of Catalyst

In a 2 L poly beaker, 1,400 g of 1,2-dimethoxyethane (manufactured by Wako Pure Chemical Industries, Ltd.) was charged and 4.82 g of zirconyl nitrate dihydrate (ZrO($NO_3$)$_2$·2H$_2$O, manufactured by Wako Pure Chemical Industries, Ltd.) was added while stirring, followed by stirring at room temperature for 5 minutes stirring. To the obtained mixed solution, 30 g of montmorillonite (Kunipia F, manufactured by KUNIMINE INDUSTRIES CO., LTD., montmorillonite containing sodium ions, potassium ions, and calcium ions as interlayer cations) was added. After stirring at room temperature for 5 minutes, a vapor phase portion in the poly beaker was replaced by nitrogen. Using a water bath, the temperature was raised to 50° C. while stirring the mixture in the poly beaker, and stirring was continued at 50° C. for 6 hours. After 6 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. to prepare a catalyst F (montmorillonite containing positively charged zirconia between layers).

Example 15

The same operation as in Example 3 was performed, except that 0.30 g of the catalyst F obtained in Reference Example 6 was used in place of 0.30 g of the catalyst A. The obtained filtrate was analyzed. As a result, the conversion ratio of cyclohexylamine was 4.8% and the selectivity of cyclohexanone oxime was 51.8%.

Reference Example 7

Preparation of Catalyst

In a 2 L poly beaker, 700 g of 1,2-dimethoxyethane (manufactured by Wako Pure Chemical Industries, Ltd.) and 15 g of Saponite (Sumecton SA, manufactured by KUNIMINE INDUSTRIES CO., LTD.) were charged. After stirring at room temperature for 5 minutes stirring, a vapor phase portion in the poly beaker was replaced by nitrogen. Using a water bath, the temperature was raised to 50° C. while stirring the mixture in the poly beaker, and 17.97 g of a 20% by weight titanium trichloride solution (dilute hydrochloric acid solution of TiCl$_3$, manufactured by Wako Pure Chemical Industries, Ltd.) was added dropwise over 1 hour. After completion of the dropwise addition, stirring was continued at 50° C. for 6 hours. After 6 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. to prepare a catalyst G (Saponite containing titanium ions between layers).

Example 16

The same operation as in Example 3 was performed, except that 0.30 g of the catalyst G obtained in Reference Example 7 was used in place of 0.30 g of the catalyst A. The obtained filtrate was analyzed. As a result, the conversion ratio of cyclohexylamine was 3.7% and the selectivity of cyclohexanone oxime was 82.0%.

Reference Example 8

Preparation of Catalyst

In a 5 L poly beaker, 2,801 g of deionized water and 71.97 g of a 20% by weight titanium trichloride solution (dilute hydrochloric acid solution of TiCl$_3$, manufactured by Wako Pure Chemical Industries, Ltd.) were charged, followed by stirring at room temperature for 5 minutes stirring. To the obtained mixed solution, 60 g of montmorillonite (Kunipia F, manufactured by KUNIMINE INDUSTRIES CO., LTD., montmorillonite containing sodium ions, potassium ions, and calcium ions as interlayer cations) was added. After stirring at room temperature for 5 minutes, a vapor phase portion in the poly beaker was replaced by nitrogen. Using a water bath, the temperature was raised to 50° C. while stirring the mixture in the poly beaker, and stirring was continued at 50° C. for 12 hours. After 12 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. to prepare a catalyst H (montmorillonite containing titanium ions between layers).

Example 17

In a reactor made of SUS316 (volume: 1 L) equipped with a thermocouple, a magnetic stirrer, a gas feed line, and a gas discharge line, 7.53 g of the catalyst H obtained in Reference Example 8, 106 g (1.1 mol) of cyclohexylamine (manufactured by Wako Pure Chemical Industries, Ltd.), and 106 g of toluene (manufactured by Wako Pure Chemical Industries, Ltd.) were charged and a vapor phase portion in the reactor was replaced by a nitrogen gas. After the reactor was sealed, a nitrogen gas was introduced into the vapor phase portion in the reactor to thereby adjust the pressure in the reactor to 0.90 MPa (gauge pressure). Next, the temperature in the reactor was raised to 80° C. while stirring. The pressure in the reactor was 0.90 MPa (gauge pressure). While continuing to stir, a mixed gas of oxygen and nitrogen (oxygen concentration: 7% by volume) was allowed to flow through the reactor by blowing into a liquid phase of the mixture in the reactor at a flow rate of 450 mL/minute to thereby initiate the reaction. While maintaining the pressure in the reactor at 0.90 MPa (gauge pressure), the reaction was continued for 5 hours while discharging the gas from the vapor phase portion in the reactor via a gas discharge line and then feed of the mixed gas of oxygen and nitrogen was stopped, followed by cooling. The obtained reaction mixture was diluted by the addition of methanol and filtrated, and then the obtained filtrate was analyzed. As a result, the conversion ratio of cyclohexylamine was 1.9% and the selectivity of cyclohexanone oxime was 60.1%.

Example 18

The same operation as in Example 17 was performed, except that temperature rise to 80° C. was replaced by temperature rise to 90° C. and the reaction was continued at 90° C. for 5 hours. The pressure in the reactor was 0.90 MPa (gauge pressure) when the temperature was raised to 90° C. The obtained filtrate was analyzed. As a result, the conversion ratio of cyclohexylamine was 2.7% and the selectivity of cyclohexanone oxime was 61.8%.

Example 19

The same operation as in Example 17 was performed, except that temperature rise to 80° C. was replaced by temperature rise to 100° C. and the reaction was continued at 100° C. for 5 hours. The pressure in the reactor was 0.90 MPa (gauge pressure) when the temperature was raised to 100° C. The obtained filtrate was analyzed. As a result, the conversion ratio of cyclohexylamine was 3.0% and the selectivity of cyclohexanone oxime was 60.3%.

Example 20

The same operation as in Example 17 was performed, except that temperature rise to 80° C. was replaced by temperature rise to 120° C. and the reaction was continued at 120° C. for 5 hours. The pressure in the reactor was 0.90 MPa (gauge pressure) when the temperature was raised to 120° C. The obtained filtrate was analyzed. As a result, the conversion ratio of cyclohexylamine was 6.2% and the selectivity of cyclohexanone oxime was 60.6%.

Reference Example 9

Preparation of Catalyst

In a 1 L poly beaker, 716.1 g of deionized water and 5.06 g of germanium tetrachloride ($GeCl_4$, manufactured by Wako Pure Chemical Industries, Ltd.) were charged, followed by stirring at room temperature for 5 minutes. To the obtained mixed solution, 15 g of montmorillonite (Kunipia F, manufactured by KUNIMINE INDUSTRIES CO., LTD., montmorillonite containing sodium ions, potassium ions, and calcium ions as interlayer cations) was added. After stirring at room temperature for 5 minutes, a vapor phase portion in the poly beaker was replaced by nitrogen. Using a water bath, the temperature was raised to 50° C. while stirring the mixture in the poly beaker, and stirring was continued at 50° C. for 12 hours. After 12 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. to prepare a catalyst I (montmorillonite containing positively charged germanium oxides between layers).

Example 21

The same operation as in Example 3 was performed, except that 0.30 g of the catalyst I obtained in Reference Example 9 was used in place of 0.30 g of the catalyst A. The obtained filtrate was analyzed. As a result, the conversion ratio of cyclohexylamine was 9.1% and the selectivity of cyclohexanone oxime was 81.0%.

Reference Example 10

In a 500 mL recovery flask, 150.2 g of deionized water and 15.1 g of the catalyst H obtained in Reference Example 8 were charged, followed by stirring at room temperature for 10 minutes. To the obtained mixture, 5.0 g of platinum nanocolloid (manufactured by Nippon Sheet Glass Co. Ltd.) was added, followed by stirring at room temperature for 5 minutes. Next, a solid was separated by distilling off water from the obtained mixture at 50° C. under reduced pressure using a rotary evaporator. This solid was calcined at 450° C. under air flow for 6 hours to prepare a catalyst J.

Example 22

The same operation as in Example 3 was performed, except that 0.31 g of the catalyst J obtained in Reference Example 10 was used in place of 0.30 g of the catalyst A. The obtained filtrate was analyzed. As a result, the conversion ratio of cyclohexylamine was 29.1% and the selectivity of cyclohexanone oxime was 90.9%.

Reference Example 11

In a 500 mL recovery flask, 50.7 g of deionized water and 5.1 g of the catalyst A obtained in Reference Example 1 was charged, followed by stirring at room temperature for 5 minutes. To the obtained mixture, 0.12 g of ruthenium chloride hydrate (manufactured by FURUYA METAL Co., Ltd., Ru content of 40.75% by weight) was added, followed by stirring at room temperature for 5 minutes. Next, a solid was separated by distilling off water from the obtained mixture at 50° C. under reduced pressure using a rotary evaporator. This solid was calcined at 450° C. under air flow for 6 hours to prepare a catalyst K.

Example 23

The same operation as in Example 1 was performed, except that 0.30 g of the catalyst K obtained in Reference Example 11 was used in place of 0.30 g of the catalyst A. The obtained filtrate was analyzed. As a result, the conversion ratio of cyclohexylamine was 2.1% and the selectivity of cyclohexanone oxime was 78.1%.

Example 24

The same operation as in Example 3 was performed, except that 0.31 g of the catalyst K obtained in Reference Example 11 was used in place of 0.30 g of the catalyst A. The obtained filtrate was analyzed. As a result, the conversion ratio of cyclohexylamine was 40.5% and the selectivity of cyclohexanone oxime was 94.9%.

Reference Example 12

The same operation as in Reference Example 11 was performed, except that 0.07 g of silver chloride (AgCl, manufactured by Wako Pure Chemical Industries, Ltd.) was used in place of 0.12 g of ruthenium chloride hydrate, a catalyst L was prepared.

Example 25

The same operation as in Example 1 was performed, except that 0.30 g of the catalyst L obtained in Reference Example 12 was used in place of 0.30 g of the catalyst A. The obtained filtrate was analyzed. As a result, the conversion ratio of cyclohexylamine was 1.6% and the selectivity of cyclohexanone oxime was 82.7%.

Example 26

The same operation as in Example 3 was performed, except that 0.30 g of the catalyst L obtained in Reference Example 12 was used in place of 0.30 g of the catalyst A. The obtained filtrate was analyzed. As a result, the conversion ratio of cyclohexylamine was 43.0% and the selectivity of cyclohexanone oxime was 94.3%.

Reference Example 13

The same operation as in Reference Example 11 was performed, except that 0.07 g of palladium chloride ($PdCl_2$, manufactured by Wako Pure Chemical Industries, Ltd.) was used in place of 0.12 g of ruthenium chloride hydrate, a catalyst M was prepared.

Example 27

The same operation as in Example 1 was performed, except that 0.30 g of the catalyst M obtained in Reference Example 13 was used in place of 0.30 g of the catalyst A. The obtained filtrate was analyzed. As a result, the conversion ratio of cyclohexylamine was 1.8% and the selectivity of cyclohexanone oxime was 83.9%.

Example 28

The same operation as in Example 3 was performed, except that 0.30 g of the catalyst M obtained in Reference Example 13 was used in place of 0.30 g of the catalyst A. The obtained filtrate was analyzed. As a result, the conversion ratio of cyclohexylamine was 38.3% and the selectivity of cyclohexanone oxime was 93.7%.

Reference Example 14

The same operation as in Reference Example 11 was performed, except that 0.10 g of iridium chloride ($IrCl_4$, manufactured by Wako Pure Chemical Industries, Ltd.) was used in place of 0.12 g of ruthenium chloride hydrate, a catalyst N was prepared.

Example 29

The same operation as in Example 3 was performed, except that 0.31 g of the catalyst N obtained in Reference Example 14 was used in place of 0.30 g of the catalyst A. The obtained filtrate was analyzed. As a result, the conversion ratio of cyclohexylamine was 42.5% and the selectivity of cyclohexanone oxime was 94.7%.

Reference Example 15

Preparation of Catalyst

In a 2 L poly beaker, 1,200 g of ethanol (manufactured by Wako Pure Chemical Industries, Ltd.) was charged and 32.13 g of a 20% by weight titanium trichloride solution (dilute hydrochloric acid solution of $TiCl_3$, manufactured by Wako Pure Chemical Industries, Ltd.) was added while stirring, followed by stirring at room temperature for 5 minutes. To the obtained mixed solution, 26.88 g of montmorillonite (Kunipia F, manufactured by KUNIMINE INDUSTRIES CO., LTD., montmorillonite containing sodium ions, potassium ions, and calcium ions as interlayer cations) was added. After stirring at room temperature for 5 minutes, a vapor phase portion in the poly beaker was replaced by nitrogen. Using a water bath, the temperature was raised to 50° C. while stirring the mixture in the poly beaker, and stirring was continued at 50° C. for 6 hours. After 6 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. and the obtained dried substance was calcined under air flow at 450° C. for 6 hours to prepare a catalyst 0.

Example 30

The same operation as in Example 3 was performed, except that 0.31 g of the catalyst 0 obtained in Reference Example 15 was used in place of 0.30 g of the catalyst A. The obtained filtrate was analyzed. As a result, the conversion ratio of cyclohexylamine was 29.3% and the selectivity of cyclohexanone oxime was 93.9%.

Reference Example 16

Preparation of Catalyst

In a 1 L poly beaker, 390 g of methanol (special grade chemical, manufactured by Wako Pure Chemical Industries, Ltd.) and 50.2 g of montmorillonite (Kunipia F, manufactured by KUNIMINE INDUSTRIES CO., LTD., montmorillonite containing sodium ions, potassium ions, and calcium ions as interlayer cations) were charged. Using a water bath, the temperature was raised to 50° C. while stirring, and 59.9 g of a 20% by weight titanium trichloride solution (dilute hydrochloric acid solution of $TiCl_3$, manufactured by Wako Pure Chemical Industries, Ltd.) was added dropwise over 1 hour. After completion of the dropwise addition, stirring was continued at 50° C. for 6 hours. After 6 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. to prepare a catalyst P (montmorillonite containing titanium ions between layers).

Example 31

The same operation as in Example 1 was performed, except that 0.30 g of the catalyst P obtained in Reference Example 16 was used in place of 0.30 g of the catalyst A. The obtained filtrate was analyzed. As a result, the conversion ratio of cyclohexylamine was 3.4% and the selectivity of cyclohexanone oxime was 82.3%.

Example 32

The same operation as in Example 3 was performed, except that 0.30 g of the catalyst P obtained in Reference Example 16 was used in place of 0.30 g of the catalyst A. The obtained filtrate was analyzed. As a result, the conversion ratio of cyclohexylamine was 27.4% and the selectivity of cyclohexanone oxime was 91.5%.

Reference Example 17

Preparation of Catalyst

In a 1 L poly beaker, 388 g of methanol (manufactured by Wako Pure Chemical Industries, Ltd.) and 50.1 g of montmorillonite (Kunipia F, manufactured by KUNIMINE INDUSTRIES CO., LTD., montmorillonite containing sodium ions, potassium ions, and calcium ions as interlayer cations) were charged. Using a water bath, the temperature was raised to 50° C. while stirring, and 62.1 g of a 30% by weight titanium sulfate solution (dilute sulfuric acid solution of $Ti(SO_4)_2$, manufactured by Wako Pure Chemical Industries, Ltd.) was added dropwise over 1 hour. After completion of the dropwise addition, stirring was continued at 50° C. for 6 hours. After 6 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. to prepare a catalyst Q (montmorillonite containing titanium ions between layers).

Example 33

The same operation as in Example 1 was performed, except that 0.30 g of the catalyst Q obtained in Reference Example 17 was used in place of 0.30 g of the catalyst A. The obtained filtrate was analyzed. As a result, the conversion ratio of cyclohexylamine was 3.1% and the selectivity of cyclohexanone oxime was 69.5%.

Example 34

The same operation as in Example 3 was performed, except that 0.30 g of the catalyst Q obtained in Reference Example 17 was used in place of 0.30 g of the catalyst A. The obtained filtrate was analyzed. As a result, the conversion ratio of cyclohexylamine was 26.4% and the selectivity of cyclohexanone oxime was 91.7%.

Reference Example 18

Preparation of Catalyst

In a 50 mL beaker, 12.1 g of ethanol (manufactured by Wako Pure Chemical Industries, Ltd.) and 6.1 g of 2 mol/L hydrochloric acid (manufactured by Wako Pure Chemical Industries, Ltd.) were charged. While stirring the obtained mixture, 25.3 g of tetraethyl orthosilicate (manufactured by Wako Pure Chemical Industries, Ltd.) was added. Using a water bath, the temperature was raised to 70° C. while stirring, and stirring was continued at 70° C. for 1 hour to prepare a solution a. Meanwhile, 36.2 g of 2 mol/L hydrochloric acid (manufactured by Wako Pure Chemical Industries, Ltd.) and 3.6 g of titanium tetraisopropoxide (manufactured by Wako Pure Chemical Industries, Ltd.) were charged in a 50 mL beaker, followed by stirring at room temperature for 1 hour to prepare a solution b.

In a 500 mL poly beaker, 187.5 g of ethanol (manufactured by Wako Pure Chemical Industries, Ltd.) and 30.5 g of montmorillonite (Kunipia F, manufactured by KUNIMINE INDUSTRIES CO., LTD., montmorillonite containing sodium ions, potassium ions, and calcium ions as interlayer cations) were charged, followed by stirring at room temperature for 5 minutes. Using a water bath, the temperature was raised to 50° C. while stirring the mixture in the poly beaker and then a mixed solution of the total amount of the solution a and the total amount of the solution b was added dropwise over 1 hour. After completion of the dropwise addition, stirring was continued at 50° C. for 6 hours. After 6 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. to prepare a catalyst R.

Example 35

The same operation as in Example 3 was performed, except that 0.30 g of the catalyst R obtained in Reference Example 18 was used in place of 0.30 g of the catalyst A. The obtained filtrate was analyzed. As a result, the conversion ratio of cyclohexylamine was 22.2% and the selectivity of cyclohexanone oxime was 89.8%.

Reference Example 19

Preparation of Catalyst

In a 50 mL beaker, 12.6 g of ethanol (manufactured by Wako Pure Chemical Industries, Ltd.) and 3.1 g of 2 mol/L hydrochloric acid (manufactured by Wako Pure Chemical Industries, Ltd.) were charged. While stirring the obtained mixture, 6.1 g of tetraethyl orthosilicate (manufactured by Wako Pure Chemical Industries, Ltd.) was added. Using a water bath, the temperature was raised to 70° C. while stirring, and stirring was continued at 70° C. for 1 hour to prepare a solution c. Meanwhile, 18.1 g of 2 mol/L hydrochloric acid (manufactured by Wako Pure Chemical Industries, Ltd.) and 1.9 g of titanium tetraisopropoxide (manufactured by Wako Pure Chemical Industries, Ltd.) were charged in a 50 mL beaker, followed by stirring at room temperature for 1 hour to prepare a solution d.

In a 300 mL poly beaker, 93.7 g of ethanol (manufactured by Wako Pure Chemical Industries, Ltd.) and 15.1 g of Saponite (Sumecton SA, manufactured by KUNIMINE INDUSTRIES CO., LTD.) were charged, followed by stirring at room temperature for 5 minutes. Using a water bath, the temperature was raised to 50° C. while stirring the mixture in the poly beaker and then a mixed solution of the total amount of the solution c and the total amount of the solution d was added dropwise over 1 hour. After completion of the dropwise addition, stirring was continued at 50° C. for 6 hours. After 6 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. to prepare a catalyst S.

Example 36

The same operation as in Example 3 was performed, except that 0.30 g of the catalyst S obtained in Reference Example 19 was used in place of 0.30 g of the catalyst A. The obtained filtrate was analyzed. As a result, the conversion ratio of cyclohexylamine was 28.4% and the selectivity of cyclohexanone oxime was 88.3%.

Reference Example 20

Preparation of Catalyst

In a 1 L poly beaker, 117 g of methanol (special grade chemical, manufactured by Wako Pure Chemical Industries, Ltd.) and 15.8 g of hectorite (LUCENTITE SWF, manufactured by Co-op Chemical Co., Ltd.) were charged. Using a water bath, the temperature was raised to 50° C. while stirring, and 18.0 g of a 20% by weight titanium trichloride solution (dilute hydrochloric acid solution of $TiCl_3$, manufactured by Wako Pure Chemical Industries, Ltd.) was added dropwise over 15 minutes. After completion of the dropwise addition, stirring was continued at 50° C. for 6 hours. After 6 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. to prepare a catalyst T (hectorite containing titanium ions between layers).

Example 37

The same operation as in Example 3 was performed, except that 0.30 g of the catalyst T obtained in Reference Example 20 was used in place of 0.30 g of the catalyst A. The obtained filtrate was analyzed. As a result, the conversion ratio of cyclohexylamine was 19.8% and the selectivity of cyclohexanone oxime was 85.2%.

Reference Example 21

Preparation of Catalyst

In a 50 mL beaker, 6.0 g of ethanol (manufactured by Wako Pure Chemical Industries, Ltd.) and 3.0 g of 2 mol/L hydrochloric acid (manufactured by Wako Pure Chemical Industries, Ltd.) were charged and 12.6 g of tetraethyl orthosilicate (manufactured by Wako Pure Chemical Industries, Ltd.) was added while stirring the obtained mixture. Using a water bath, the temperature was raised to 70° C. while stirring and stirring was continued at 70° C. for 1 hour to prepare a solution e. Meanwhile, 18.0 g of 2 mol/L hydrochloric acid (manufactured by Wako Pure Chemical Industries, Ltd.) and 1.8 g of titanium tetraisopropoxide (manufactured by Wako Pure Chemical Industries, Ltd.) were charged in a 50 mL beaker, followed by stirring at room temperature for 1 hour to prepare a solution f.

In a 500 mL poly beaker, 93.6 g of ethanol (manufactured by Wako Pure Chemical Industries, Ltd.) and 15.0 g of hectorite (LUCENTITE SWF, manufactured by Co-op Chemical Co., Ltd.) were charged, followed by stirring at room temperature for 5 minutes. Using a water bath, the temperature was raised to 50° C. while stirring the mixture in the poly beaker and then a mixed solution of the total amount of the solution e and the total amount of the solution f was added dropwise over 1 hour. After completion of the dropwise addition, stirring was continued at 50° C. for 6 hours. After 6 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. to prepare a catalyst U.

Example 38

The same operation as in Example 3 was performed, except that 0.30 g of the catalyst U obtained in Reference Example 21 was used in place of 0.30 g of the catalyst A. The obtained filtrate was analyzed. As a result, the conversion ratio of cyclohexylamine was 20.5% and the selectivity of cyclohexanone oxime was 88.7%.

Reference Example 22

Preparation of Catalyst

In a 1 L poly beaker, 156 g of methanol (special grade chemical, manufactured by Wako Pure Chemical Industries, Ltd.) and 20.0 g of stevensite (Sumecton ST, manufactured by KUNIMINE INDUSTRIES CO., LTD.) were charged. Using a water bath, the temperature was raised to 50° C. while stirring, and 24.0 g of 20% by weight titanium trichloride solution (dilute hydrochloric acid solution of $TiCl_3$, manufactured by Wako Pure Chemical Industries, Ltd.) was added dropwise over 25 minutes. After completion of the dropwise addition, stirring was continued at 50° C. for 6 hours. After 6 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. to prepare a catalyst V (stevensite containing titanium ions between layers).

Example 39

The same operation as in Example 3 was performed, except that 0.30 g of the catalyst V obtained in Reference Example 22 was used in place of 0.30 g of the catalyst A. The obtained filtrate was analyzed. As a result, the conversion ratio of cyclohexylamine was 17.1% and the selectivity of cyclohexanone oxime was 86.2%.

Reference Example 23

Preparation of Catalyst

In a 100 mL beaker, 15.9 g of methanol (manufactured by Wako Pure Chemical Industries, Ltd.) and 8.0 g of 2 mol/L hydrochloric acid (manufactured by Wako Pure Chemical Industries, Ltd.) were charged, and 33.6 g of tetraethyl orthosilicate (manufactured by Wako Pure Chemical Industries, Ltd.) was added while stirring the obtained mixture. Using a water bath, the temperature was raised to 70° C. while stirring and stirring was continued at 70° C. for 1 hour to prepare a solution g. Meanwhile, 48.0 g of 2 mol/L hydrochloric acid (manufactured by Wako Pure Chemical Industries, Ltd.) and 4.8 g of titanium tetraisopropoxide (manufactured by Wako Pure Chemical Industries, Ltd.) were charged in a 100 mL beaker, followed by stirring at room temperature for 1 hour to prepare a solution h.

In a 1 L poly beaker, 250 g of methanol (manufactured by Wako Pure Chemical Industries, Ltd.) and 40.0 g of stevensite (Sumecton ST, manufactured by KUNIMINE INDUSTRIES CO., LTD.) were charged, followed by stirring at room temperature for 5 minutes. Using a water bath, the temperature was raised to 50° C. while stirring the mixture in the poly beaker and then a mixed solution of the total amount of the solution g and the total amount of the solution h was added dropwise over 1 hour. After completion of the dropwise addition, stirring was continued at 50° C. for 6 hours. After 6 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. to prepare a catalyst W.

Example 40

The same operation as in Example 3 was performed, except that 0.30 g of the catalyst W obtained in Reference Example 23 was used in place of 0.30 g of the catalyst A. The obtained filtrate was analyzed. As a result, the conversion ratio of cyclohexylamine was 11.5% and the selectivity of cyclohexanone oxime was 93.7%.

Reference Example 24

In a 1 L recovery flask, 200 g of deionized water and 0.51 g of ruthenium chloride hydrate (manufactured by FURUYA METAL Co., Ltd., Ru content: 40.75% by weight) were charged, followed by stirring at room temperature for 5 minutes. To the obtained mixture, 20.1 g of the catalyst P obtained in Reference Example 16 was added, followed by stirring at room temperature for 1 hour. Next, a solid was separated by distilling off water from the obtained mixture at 50° C. under reduced pressure using a rotary evaporator. This solid was calcined at 450° C. under air flow at a flow rate of 50 mL/minute for 6 hours to prepare a catalyst X.

Example 41

The same operation as in Example 3 was performed, except that 0.30 g of the catalyst X obtained in Reference Example 24 was used in place of 0.30 g of the catalyst A. The obtained filtrate was analyzed. As a result, the conversion ratio of cyclohexylamine was 38.1% and the selectivity of cyclohexanone oxime was 93.6%.

Reference Example 25

In a 500 mL recovery flask, 50.5 g of deionized water and 0.12 g of nickel(II) chloride (anhydrous, $NiCl_2$, manufactured by Wako Pure Chemical Industries, Ltd.) were charged, followed by stirring at room temperature for 5 minutes. To the obtained mixture, 5.0 g of the catalyst P obtained in Reference Example 16 was added, followed by stirring at room temperature for 1 hour. Next, a solid was separated by distilling off water from the obtained mixture at 50° C. under reduced pressure using a rotary evaporator. This solid was calcined at 450° C. under air flow at a flow rate of 50 mL/minute for 6 hours to prepare a catalyst Y.

Example 42

The same operation as in Example 1 was performed, except that 0.30 g of the catalyst Y obtained in Reference Example 25 was used in place of 0.30 g of the catalyst A. The obtained filtrate was analyzed. As a result, the conversion ratio of cyclohexylamine was 0.3% and the selectivity of cyclohexanone oxime was 61.1%.

Example 43

The same operation as in Example 3 was performed, except that 0.30 g of the catalyst Y obtained in Reference Example 25 was used in place of 0.30 g of the catalyst A. The obtained filtrate was analyzed. As a result, the conversion ratio of cyclohexylamine was 34.2% and the selectivity of cyclohexanone oxime was 94.6%.

Reference Example 26

The same operation as in Reference Example 25 was performed, except that 0.10 g of gold(III) chloride acid tetrahydrate ($HAuCl_4.4H_2O$, manufactured by Kanto Chemical Co., Inc.) was used in place of 0.12 g of nickel (II) chloride, a catalyst Z was prepared.

Example 44

The same operation as in Example 1 was performed, except that 0.30 g of the catalyst Z obtained in Reference Example 26 was used in place of 0.30 g of the catalyst A. The obtained filtrate was analyzed. As a result, the conversion ratio of cyclohexylamine was 2.1% and the selectivity of cyclohexanone oxime was 82.7%.

Example 45

The same operation as in Example 3 was performed, except that 0.30 g of the catalyst Z obtained in Reference Example 26 was used in place of 0.30 g of the catalyst A. The obtained filtrate was analyzed. As a result, the conversion ratio of cyclohexylamine was 31.2% and the selectivity of cyclohexanone oxime was 91.7%.

Reference Example 27

In a 200 mL recovery flask, 40.0 g of deionized water and 1.14 g of aluminum nitrate octahydrate ($Al(NO_3)_3.9H_2O$, manufactured by Wako Pure Chemical Industries, Ltd.) were charged, followed by stirring at room temperature to obtain a solution. To the obtained solution, 4.0 g of the catalyst P obtained in Reference Example 16 was added and then a mixed solution of 0.36 g of sodium hydroxide (manufactured by Wako Pure Chemical Industries, Ltd.) and 30.0 g of deionized water was added dropwise, followed by stirring at room temperature for 2 hours. Next, a solid was separated by pressure filtration of the obtained mixture, and this solid was washed with 400 mL of water and filtered by pressure filtration. After washing, the obtained solid was dried overnight at 110° C. and the obtained dried substance was calcined at 200° C. under air flow at a flow rate of 50 mL/minute for 6 hours to prepare a catalyst a.

Example 46

The same operation as in Example 3 was performed, except that 0.30 g of the catalyst a obtained in Reference Example 27 was used in place of 0.30 g of the catalyst A. The obtained filtrate was analyzed. As a result, the conversion ratio of cyclohexylamine was 28.1% and the selectivity of cyclohexanone oxime was 93.1%.

Comparative Example 1

The same operation as in Example 1 was performed, except that 0.30 g of titanium oxide (TiO$_2$, ST-01, manufactured by ISHIHARA SANGYO KAISHA, LTD.) was used in place of 0.30 g of the catalyst A. The obtained filtrate was analyzed. As a result, the conversion ratio of cyclohexylamine was 0.2% and the selectivity of cyclohexanone oxime was 5.6%.

Comparative Example 2

The same operation as in Example 3 was performed, except that 0.30 g of titanium oxide (TiO$_2$, ST-01, manufactured by ISHIHARA SANGYO KAISHA, LTD.) was used in place of 0.30 g of the catalyst A. The obtained filtrate was analyzed. As a result, the conversion ratio of cyclohexylamine was 3.1% and the selectivity of cyclohexanone oxime was 46.3%.

Comparative Example 3

The same operation as in Example 17 was performed, except that 7.50 g of titanium oxide (TiO$_2$, ST-01, manufactured by ISHIHARA SANGYO KAISHA, LTD.) was used in place of 7.53 g of the catalyst H. The obtained filtrate was analyzed. As a result, the conversion ratio of cyclohexylamine was 0.2% and the selectivity of cyclohexanone oxime was 10.6%.

The invention claimed is:

1. A method for producing an oxime represented by the following formula (II):

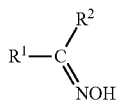
(II)

wherein R$^1$ and R$^2$ are respectively the same as defined below, the method comprising oxidizing an amine represented by the following formula (I):

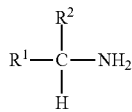
(I)

wherein R$^1$ and R$^2$ each independently represents a hydrogen atom, an optionally substituted hydrocarbon group, or an optionally substituted heterocyclic group (provided that R$^1$ and R$^2$ are not simultaneously hydrogen atoms), or R$^1$ and R$^2$, together with the carbon atom to which R$^1$ and R$^2$ are attached, form an optionally substituted alicyclic hydrocarbon group having 3 to 12 carbon atoms, with oxygen in the presence of a layered silicate.

2. The method according to claim 1, wherein the layered silicate is smectite.

3. The method according to claim 1, wherein the layered silicate contains at least one selected from the group consisting of hydrogen ions, ammonium ions, quaternary ammonium ions, cations of group 4 metal elements, cations of group 5 metal elements, cations of group 6 metal elements, germanium ions, oxides of positively charged group 4 metal elements, oxides of positively charged group 5 metal elements, oxides of positively charged group 6 metal elements, and positively charged germanium oxides.

4. The method according to claim 1, wherein the layered silicate contains at least one selected from the group consisting of cations of group 4 metal elements, germanium ions, oxides of positively charged group 4 metal elements, and positively charged germanium oxides.

5. The method according to claim 1, wherein the layered silicate contains at least one selected from the group consisting of titanium ions, germanium ions, positively charged titanium oxides, and positively charged germanium oxides.

6. The method according to claim 3, wherein the layered silicate further contains at least one selected from the group consisting of cations of group 8 metal elements, cations of group 9 metal elements, cations of group 10 metal elements, cations of group 11 metal elements, cations of group 12 metal elements, cations of group 13 metal elements, oxides of positively charged group 8 metal elements, oxides of positively charged group 9 metal elements, oxides of positively charged group 10 metal elements, oxides of positively charged group 11 metal elements, oxides of positively charged group 12 metal elements, oxides of positively charged group 13 metal elements, and oxides of positively charged silicon.

7. The method according to claim 1, wherein the layered silicate is calcined at 150° C. to 600° C.

* * * * *